(12) United States Patent
Hassell et al.

(10) Patent No.: US 8,629,330 B2
(45) Date of Patent: Jan. 14, 2014

(54) METHODS AND COMPOSITIONS FOR THE INHIBITION OF MERISTEMATIC GROWTH ON CUCURBIT ROOTSTOCK

(71) Applicant: Syngenta Participations AG, Basel (CH)

(72) Inventors: Richard Hassell, Charleston, SC (US); James Brusca, Woodland, CA (US); Xingping Zhang, Woodland, CA (US); Shawna Daley, Charleston, SC (US)

(73) Assignees: Syngenta Participations AG, Basel (CH); Clemson University, Anderson, SC (US)

( * ) Notice: Subject to any disclaimer, the term of this patent is extended or adjusted under 35 U.S.C. 154(b) by 0 days.

(21) Appl. No.: 13/762,002

(22) Filed: Feb. 7, 2013

(65) Prior Publication Data
US 2013/0312139 A1 Nov. 21, 2013

Related U.S. Application Data

(60) Provisional application No. 61/647,312, filed on May 15, 2012.

(51) Int. Cl.
*A01H 5/00* (2006.01)
*A01H 4/00* (2006.01)
*A01H 5/04* (2006.01)

(52) U.S. Cl.
USPC ............ 800/308; 800/307; 800/295; 800/269

(58) Field of Classification Search
None
See application file for complete search history.

(56) References Cited

U.S. PATENT DOCUMENTS

| | | | |
|---|---|---|---|
| 3,438,765 A | 4/1969 | Tso | |
| 3,598,564 A | 8/1971 | Jacobi et al. | |
| 4,077,795 A * | 3/1978 | Cooke et al. | 504/186 |
| 4,077,796 A | 3/1978 | Kish | |
| RE30,216 E | 2/1980 | Kish | |
| 4,219,350 A | 8/1980 | Barer | |
| 4,272,277 A | 6/1981 | Barer | |
| 4,522,644 A * | 6/1985 | Young | 504/186 |
| 6,245,712 B1 | 6/2001 | Wiley et al. | |

OTHER PUBLICATIONS

Yanhong et al (2009 J. Plant Res 122:529-540.*
Vegetable Grafting Symposium—Posters and Presentation, "Development of Grafting Technology to Improve Sustainability and Competitiveness of the US Fruiting Vegetable Industry", Maitland, Florida, Nov. 8, 2012, 5 Pages.
Daley S. and Hassell R. ., "Fatty Alcohol Application Increases Total Nonstructural Carbohydrates in Rootstock Seedlings.", Vegetable Grafting Symposium, Maitland, Florida, Nov. 8, 2012, 18 Pages.
Daley S. and Hassell R., "Fatty Alcohol Treatments Control Rootstock Re-growth in Grafted Watermelon", Vegetable Grafting Symposium, Maitland, Florida, Nov. 8, 2012, 1 Page.
Hassell, R. "Effects of Grafted Watermelon Transplants on Fruit Yields, Holding Ability in the Field and Post-Harvest Fruit Quality", Vegetable Grafting Symposium, Maitland, Florida, Nov. 8, 2012, 45 Pages.
Zhao D. et al., "Rapid Analysis of Nonstructural Carbohydrate Components in Grass Forage Using Microplate Enzymatic Assays", *Crop Sci.*, 50:1537-1545, 2010.
Choi, D.C. et al., "Using Chemical Controls to Inhibited Axillary Buds of *Lagernaria* as Rootstock for Grafted Watermelon (*Citrullus lanatus*)", *Acta Hort (ISHS)*, 588:43-48, (2002).
Fair 85 Label, Fair Products Inc., Printed from the internet Mar. 2, 2012 at URL http://iaspub.epa.gov/apex/pesticides/f?p=PPLS:102:::NO::P102_REG_NUM:51873-7.
Off-Shoot-T Label, Chemtura Corp., 2009, Tobacco sucker Control Agent High Active Formula.
Sucker-Plucker Concentrate Label, Drexel Chemical Company, Printed from the internet Mar. 2012 at URL http://www.drexchem.com/Products/Labels/Drexel_Sucker-Plucker_10063_LABEL.pdf.
Virginia Bright Flue-Cured Tobacco Board, 2012 Flue-Cured Tobacco Production Guide, Revised Dec. 2011, Publication 436-048, 138 pages (See p. 36).
Memmott, "Refinement of Innovative Watermelon Grafting Methods with Appropriate Choice of Developmental Stage, Rootstock Genotype, and Root Treatment to Increase Grafting Success", Thesis, Graduate School of Clemson University, May 2010, 108 Pages.
International Search Report and Written Opinion Corresponding to International Application No. PCT/US2013/040763; Date of Mailing: Oct. 8, 2013; 11 Pages.

* cited by examiner

*Primary Examiner* — Brent T Page
(74) *Attorney, Agent, or Firm* — Myers Bigel Sibley & Sajovec, PA

(57) ABSTRACT

The invention provides methods of inhibiting the growth of a shoot apical meristem of a cucurbit rootstock plant, comprising contacting a shoot apical meristem of the cucurbit rootstock plant with an effective amount of a composition comprising one or more fatty alcohols, thereby inhibiting the growth of the shoot apical meristem of the cucurbit rootstock plant. The present invention further provides methods for preparing and producing cucurbit rootstock plants for grafting and methods for grafting. Additionally provided are cucurbit rootstock plants and plant parts and grafted cucurbit plants produced by the methods of the invention.

28 Claims, 15 Drawing Sheets

METHODS AND COMPOSITIONS FOR THE INHIBITION OF MERISTEMATIC GROWTH ON CUCURBIT ROOTSTOCK

STATEMENT OF PRIORITY

This application claims the benefit, under 35 U.S.C. §119(e), of U.S. Provisional Application No. 61/647,312, filed May 15, 2012, the entire contents of which is incorporated by reference herein.

FIELD OF THE INVENTION

The present invention relates to compositions and methods for inhibiting the shoot apical meristem of cucurbit rootstock plants.

BACKGROUND OF THE INVENTION

Cultivated crops in the plant family Cucurbitaceae such as watermelon, squash, cucumber and melon have been using grafted plants for commercial production in many production areas. This is done to overcome problems related to soil borne pathogens, abiotic stress and for improvement in yield and fruit quality, and for extension of the growing season. Consequently, there is a strong demand in many parts of the world for grafted cucurbit plants, including Asia, Europe, the United States of America and Mexico. However, grafting cucurbits is a labor intensive process which requires a skilled, efficient, and consistent labor force. The cost and quality of grafted plants are key input cost for production.

Typically, the rootstock varieties (*Lagenaria* spp., interspecific squash hybrids, wax gourds or wild watermelon) used in grafting produce much more vigorous plants than scion plants, and thus the shoot growth of the rootstock on grafted plant can outcompete the scion for light, water and nutrients. Consequently, the standard practice is to remove by hand the shoot tip of rootstock in the seedling tray before grafting and again before grafts leave the transplant house. The grower then needs to scout fields and further hand prune rootstock shoot growth in the field for a period of time to eliminate any shoots of the rootstock plants that were missed or have regrown. Failure to remove rootstock shoots can adversely affect the development of grafts in transplant production, the establishment of grafted plants in the field, and the productivity of grafted plants due to the competition by the vigorous rootstock shoots that remain and are allowed to grow.

This repeated pruning can represent a significant labor need and expense to the grower and is particularly limiting in areas where labor costs are high, such as in the U.S. Currently, in Mexico, growers are able to commercially supply grafted watermelon plants, but in the U.S., grafted cucurbit plants are not produced on a commercial scale. Phytosanitary import restrictions prevent the movement of soil (or seedlings in soil) from Mexico to the USA, therefore, the U.S. commercial production cannot easily use grafted plants produced in Mexico.

The present invention overcomes the shortcomings in the field by providing alternative methods for inhibiting the shoot apical meristem of a cucurbit rootstock plant to be used in grafting procedures.

SUMMARY OF THE INVENTION

One aspect of the present invention provides a method of inhibiting the growth of a shoot apical meristem of a cucurbit plant, comprising contacting a shoot apical meristem of the cucurbit plant with an effective amount of a composition comprising one or more fatty alcohols, thereby inhibiting the growth of the shoot apical meristem of the cucurbit plant. In some aspects, the cucurbit plant is a cucurbit rootstock plant.

In other aspects, the present invention provides a method of producing a cucurbit rootstock plant for grafting, comprising contacting a shoot apical meristem of a cucurbit rootstock plant with an effective amount of a composition comprising one or more fatty alcohols prior to grafting, thereby inhibiting the growth of the shoot apical meristem of the cucurbit rootstock plant and producing a cucurbit rootstock plant for grafting.

A further aspect of the invention provides a method of producing a grafted cucurbit plant, comprising (a) contacting a shoot apical meristem of a cucurbit rootstock plant with an effective amount of a composition comprising one or more fatty alcohols; and (b) grafting a cucurbit scion onto the cucurbit rootstock plant of (a), thereby producing a grafted cucurbit plant.

A further aspect of the invention provides a method of increasing the amount of at least one nonstructural carbohydrate in a cucurbit plant, comprising contacting a shoot apical meristem of the cucurbit plant with an effective amount of a composition comprising one or more fatty alcohols, thereby inhibiting the growth of the shoot apical meristem and increasing the amount of at least one nonstructural carbohydrate in the cucurbit plant. In some aspects, the cucurbit plant is a cucurbit rootstock plant. In other embodiments, the at least one nonstructural carbohydrate comprises total nonstructural carbohydrates.

The present invention further provides a method of grafting a cucurbit scion onto a cucurbit rootstock plant, comprising contacting a shoot apical meristem of a cucurbit rootstock plant with an effective amount of a composition comprising one or more fatty alcohols; and (b) grafting a cucurbit scion onto the cucurbit rootstock plant of (a).

In other aspects, the present invention provides a method of increasing grafting success rate between a cucurbit rootstock plant and a cucurbit scion plant, comprising (a) inhibiting the growth of a shoot apical meristem of the cucurbit rootstock plant by contacting a shoot apical meristem of the cucurbit rootstock plant with an effective amount of a composition comprising one or more fatty alcohols prior to grafting; and (c) grafting a cucurbit scion onto the cucurbit rootstock plant of (a), wherein the grafting success rate of the rootstock to the scion is increased.

In still other aspects of the invention, the composition comprising one or more fatty alcohol comprises N-hexanol ($C_6$) fatty alcohol, N-heptanol ($C_7$) fatty alcohol, N-octanol ($C_8$) fatty alcohol, N-nonanol ($C_9$) fatty alcohol, N-decanol ($C_{10}$) fatty alcohol, N-undecanol ($C_{11}$) fatty alcohol, N-dodecanol ($C_{12}$), N-tridecanol ($C_{13}$) fatty alcohol, N-tetradecanol ($C_{14}$) fatty alcohol, N-pentadecanol ($C_{15}$) fatty alcohol, N-hexadecanol ($C_{16}$) fatty alcohol, N-heptadecanol ($C_{17}$) fatty alcohol, N-octadecanol ($C_{18}$) fatty alcohol, N-nonadecanol ($C_{19}$) fatty alcohol, N-eicosanol ($C_{20}$) fatty alcohol, and/or any combination thereof. In other aspects of the invention, the composition comprising one or more fatty alcohol comprises N-hexanol fatty alcohol ($C_6$), N-octanol ($C_8$) fatty alcohol, N-decanol ($C_{10}$) fatty alcohol, N-dodecanol ($C_{12}$), N-tetradecanol, or any combination thereof. In further aspects of the invention, the composition comprising one or more fatty alcohols comprises N-octanol ($C_8$) fatty alcohol, N-decanol ($C_{10}$) fatty alcohol, or a combination thereof. In still further aspects of the invention, the concentration of the one or more fatty alcohols in the composition can be about 2.0% (v/v) to about 40% (v/v).

In further aspects of the invention, the cucurbit rootstock plant is a wild watermelon rootstock plant, a bottle gourd rootstock plant, *Lagenaria siceraria*, an interspecific squash rootstock plant, figleaf gourd, wax gourd, *C. moschata, Cucumis hystrix* Chakrav. *Cucumis hytivus* J. F. Chen & J. H. Kirkbr, *Cucumis metuliferus* E. Mey. ex Naud., *Cucumis melo*, and/or other suitable wild-type cucurbit.

The present invention further provides cucurbit rootstock plants and plant parts and grafted cucurbit plants produced using the methods described herein The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

DETAILED DESCRIPTION OF THE INVENTION

Figure 1:
FIG. 1 shows the problem of shoot regrowth after manually removing the shoot apical meristem in a cucurbit rootstock plant.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage, an amount or a time period and the like, is meant to encompass variations of ±20%, ±10%, ±5%, ±1%, ±0.5%, or even ±0.1% of the specified amount (e.g., an amount of one or more fatty alcohol).

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the phrase "inhibit the shoot apical meristem" or "inhibiting the shoot apical meristem" and grammatical variations thereof, refers to reducing the growth of the shoot apical meristem by burning, desiccating, destroying, removing and/or killing the shoot apical meristem.

As used herein, the terms "inhibit," "inhibits," "inhibited," "inhibition" and similar terms used in reference to the growth of the shoot apical meristem mean a decrease or reduction in growth of the shoot apical meristem of at least about 20%, 25%, 30%, 35%, 40%, 45%, 50%, 55%, 60%, 75%, 80%, 85%, 90%, 95%, 100% as compared to a control (e.g., a rootstock plant that has not been treated with a composition comprising one or more fatty alcohols). In particular embodiments, the inhibition results in no or essentially no (i.e., an insignificant amount, e.g., less than about 10%, less than about 5% or even less than about 1%) detectable growth of the shoot apical meristem.

Current practices of preparing cucurbit rootstock incur significant labor costs due to the need to hand prune rootstock shoot growth. Hand pruning is not only time consuming but often ineffective due to regrowth of the apical shoot (See, FIG. 1). Thus, using manual methods, the pruning must be done prior to grafting and then again in the field to again eliminate any shoots of the rootstock that were missed or regrow after grafting. Typically, the rootstock plants are quite vigorous in comparison to the scion plants and as a result, if rootstock shoots are not removed, their relatively greater vigor can adversely affect the development of grafts in transplant production, the establishment of grafted plants in field, and the productivity of grafted plants. The present invention provides an economical alternative to hand pruning of a cucurbit shoot apical meristem by providing a chemical means of eliminating the cucurbit rootstock shoot apical meristem.

The methods of the present invention for removing a cucurbit meristem are more effective than previous methods because the methods of the invention using fatty alcohol can result in complete removal of the meristem without damage to the hypocotyl. Other methods such as manual removal of the meristem (cutting) or other chemicals are either not complete (only a single cell left behind allows for regrowth) or damage the rootstock too much for it to survive and be useful in grafting.

Figure 2:
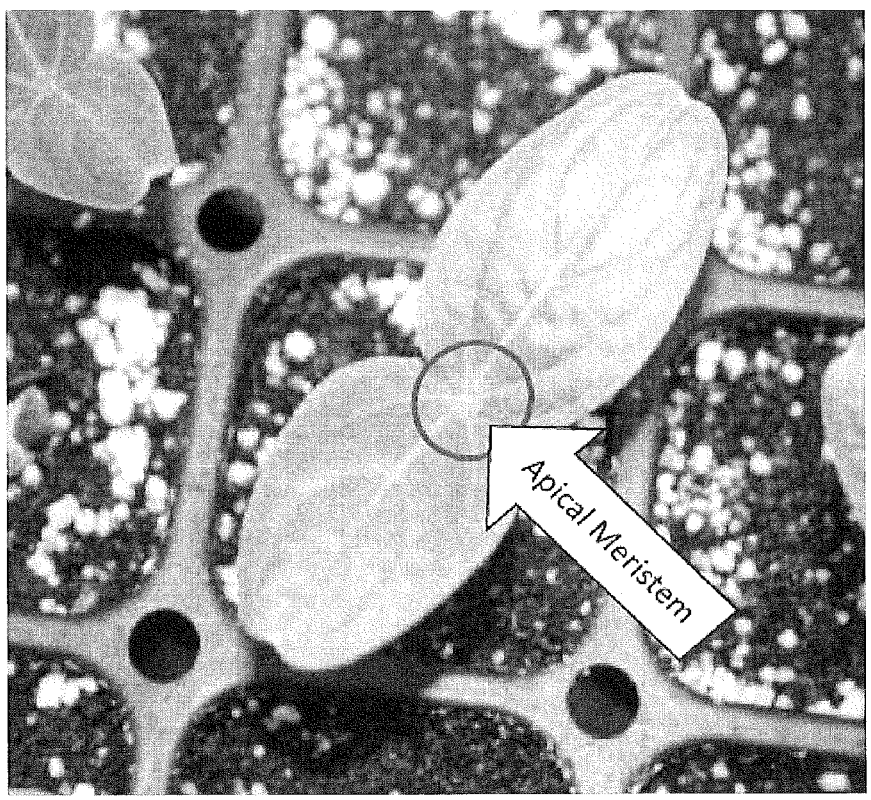
FIG. 2 shows the growing point of the cucurbit rootstock plant.
Figure 3:
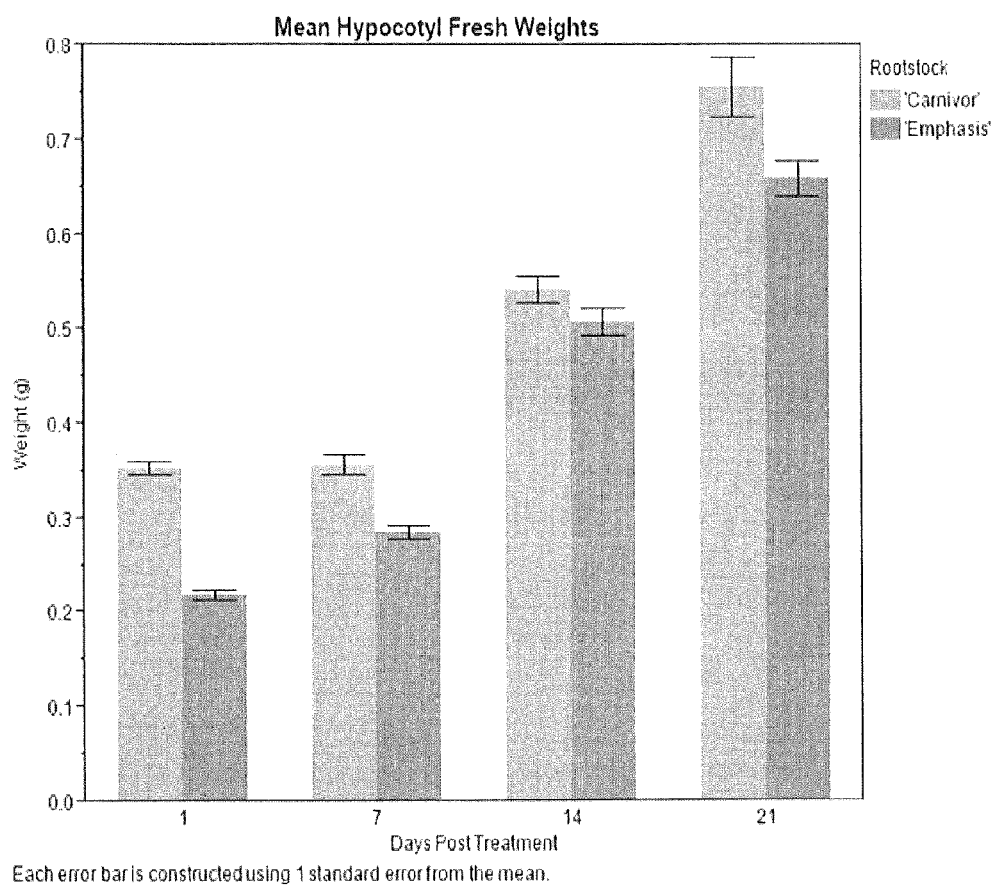
FIG. 3 shows the mean hypocotyl fresh weight for the 'Carnivor' interspecific hybrid squash and 'Emphasis' bottle gourd rootstock seedlings following treatment with the fatty alcohol.
Figure 4:
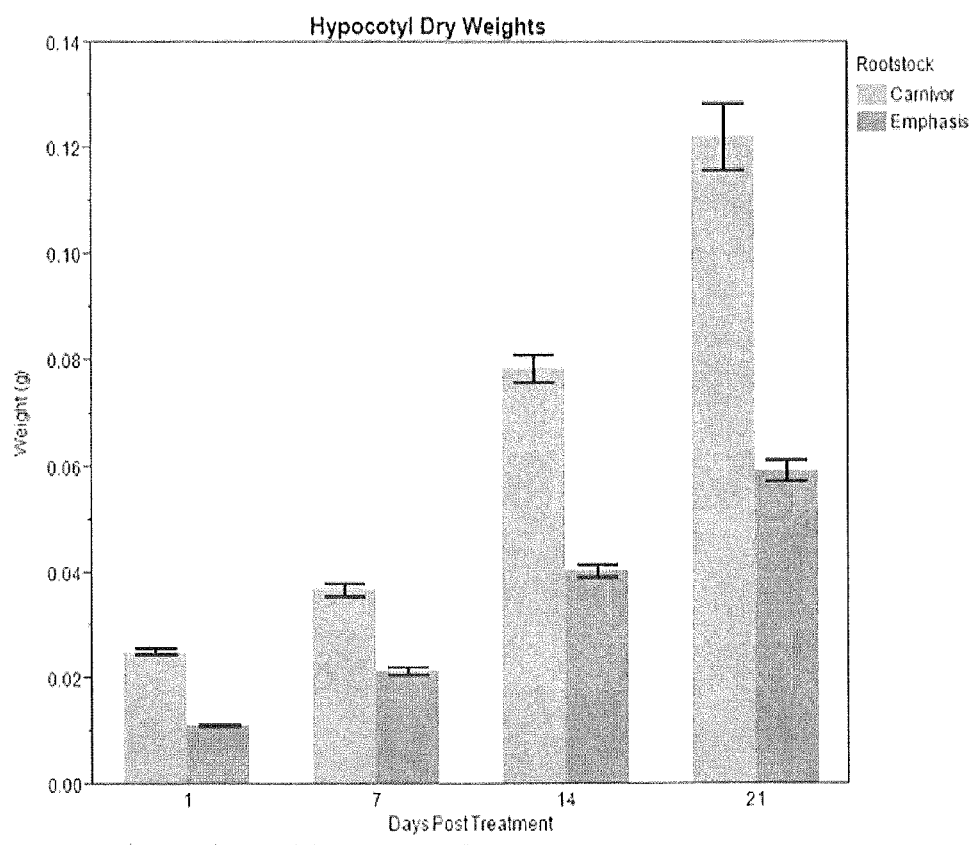
FIG. 4 shows the hypocotyl dry weights for the 'Carnivor' interspecific hybrid squash and 'Emphasis' bottle gourd rootstock seedlings following treatment with the fatty alcohol.
Figure 5:
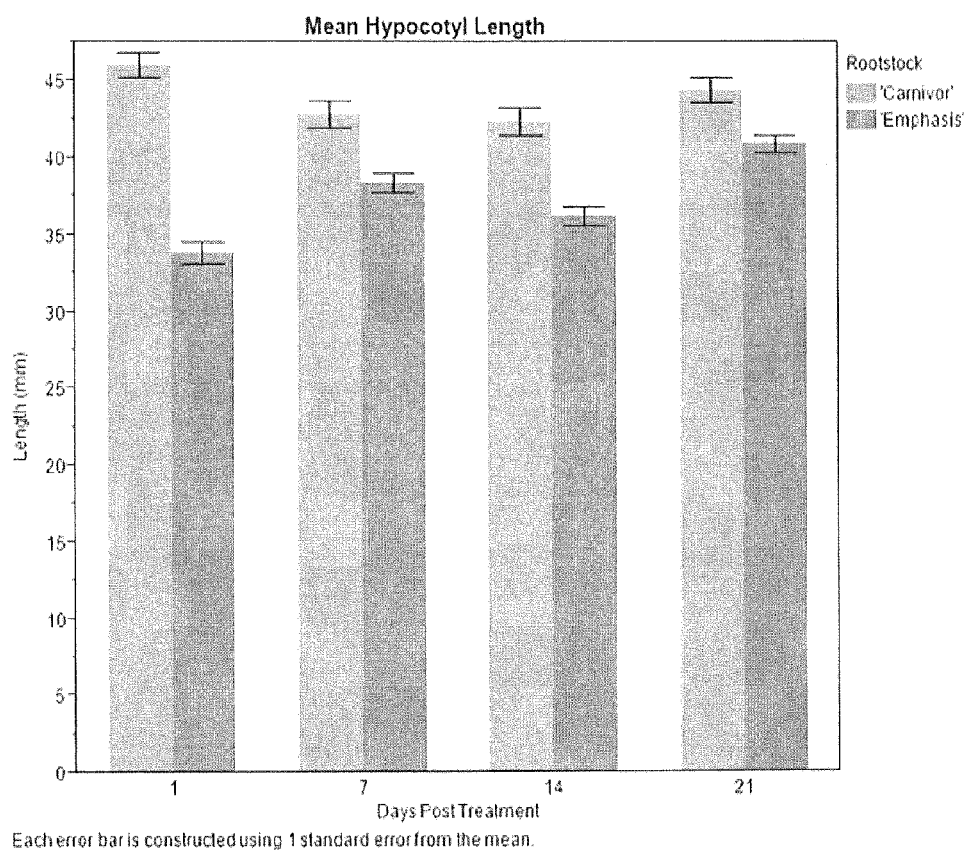
FIG. 5 shows the mean hypocotyl length for the 'Carnivor' interspecific hybrid squash and 'Emphasis' bottle gourd rootstock seedlings following treatment with the fatty alcohol.
Figure 6:
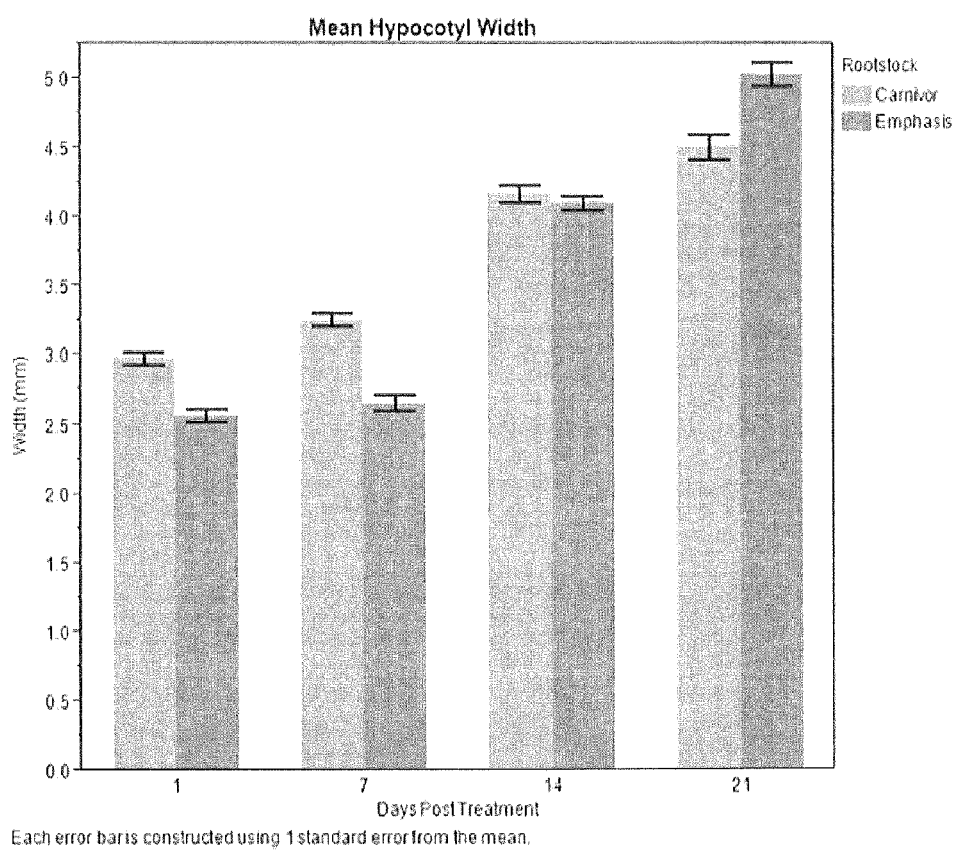
FIG. 6 shows the mean hypocotyl width for the 'Carnivor' interspecific hybrid squash and 'Emphasis' bottle gourd rootstock seedlings following treatment with the fatty alcohol.
Figure 7:
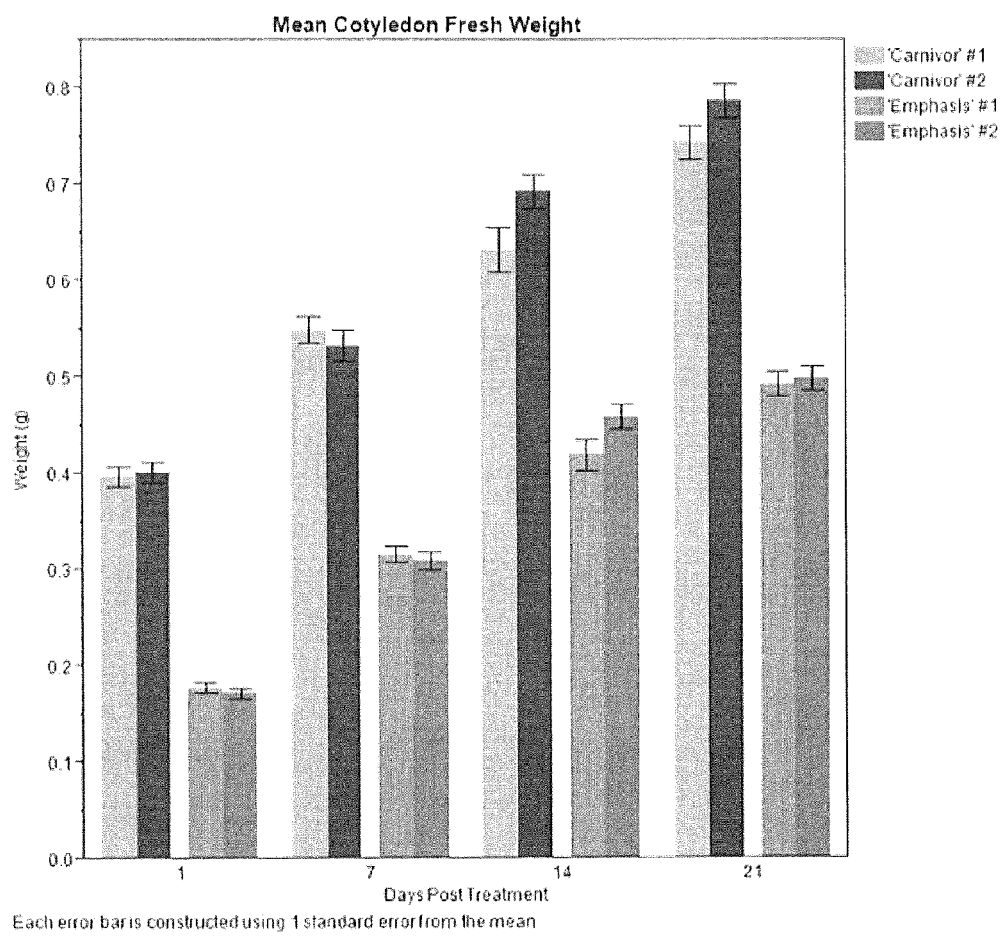
FIG. 7 shows the mean cotyledon fresh weight for the 'Carnivor' interspecific hybrid squash and 'Emphasis' bottle gourd rootstock seedlings following treatment with the fatty alcohol.
Figure 8:
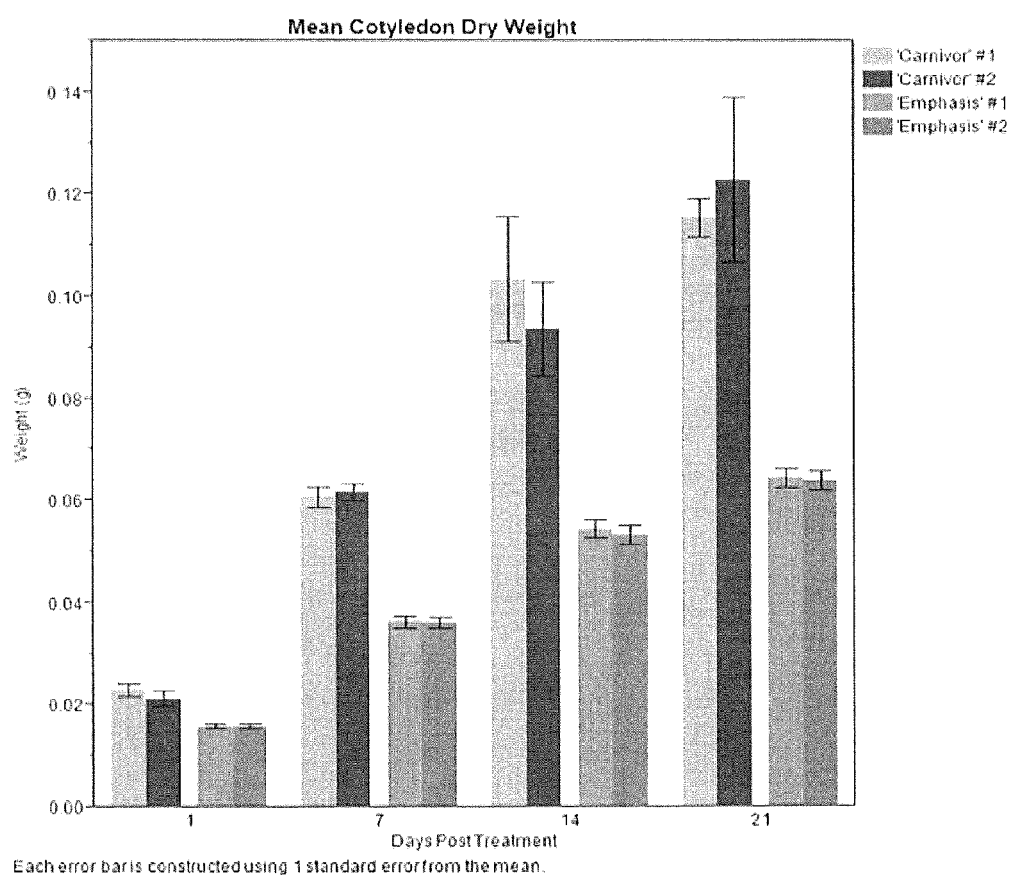
FIG. 8 shows the mean cotyledon dry weight for the 'Carnivor' interspecific hybrid squash and 'Emphasis' bottle gourd rootstock seedlings following treatment with the fatty alcohol.
Figure 9:
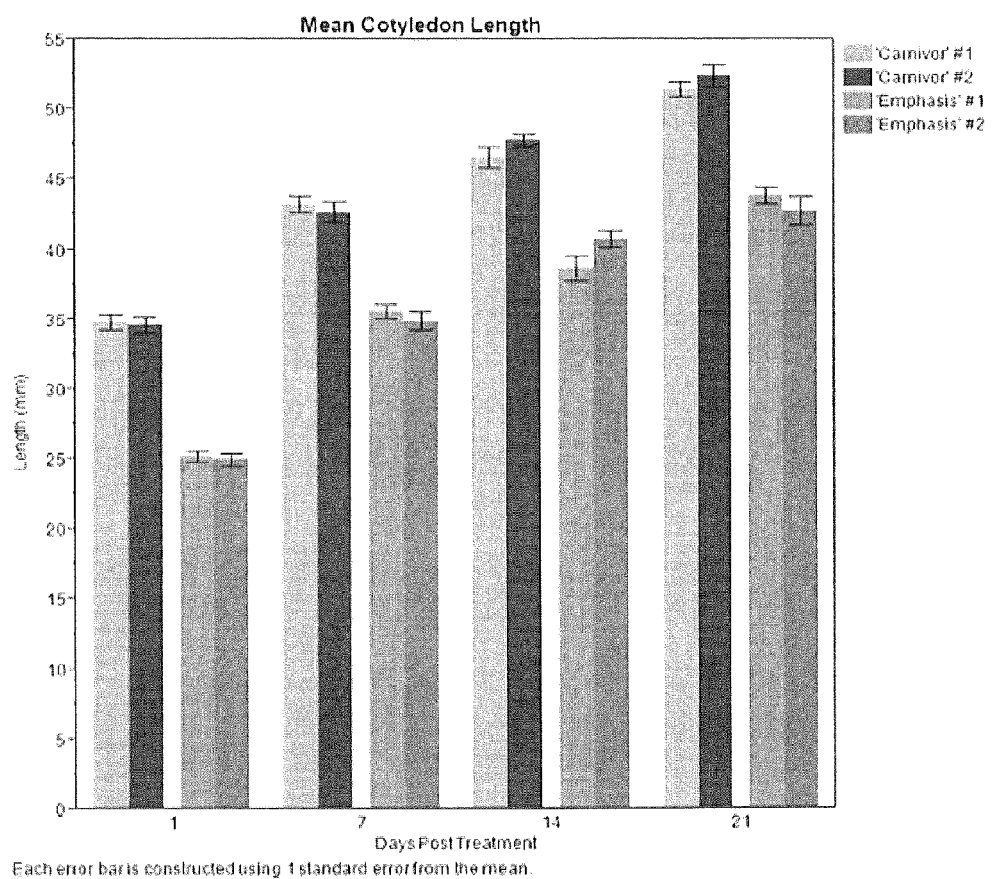
FIG. 9 shows the mean cotyledon length for the 'Carnivor' interspecific hybrid squash and 'Emphasis' bottle gourd rootstock seedlings following treatment with the fatty alcohol.
Figure 10:
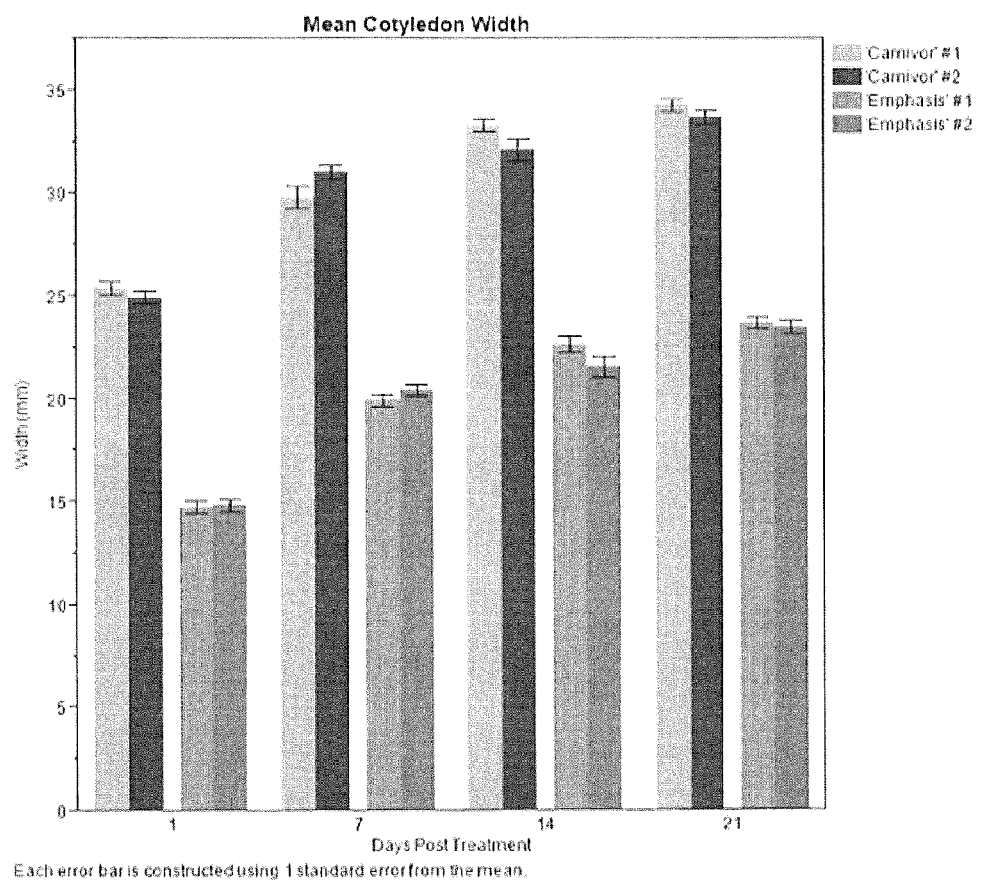
FIG. 10 shows the mean cotyledon width for the 'Carnivor' interspecific hybrid squash and 'Emphasis' bottle gourd rootstock seedlings following treatment with the fatty alcohol.
Figure 11:
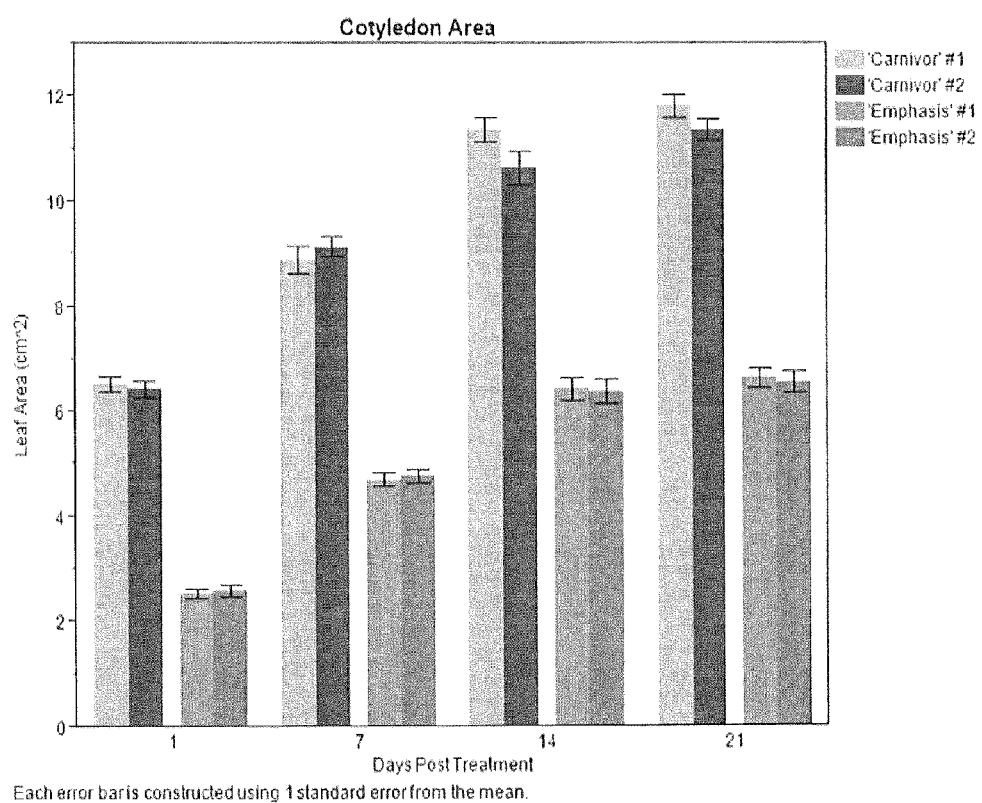
FIG. 11 shows the cotyledon area for the 'Carnivor' interspecific hybrid squash and 'Emphasis' bottle gourd rootstock seedlings following treatment with the fatty alcohol.
Figure 12:
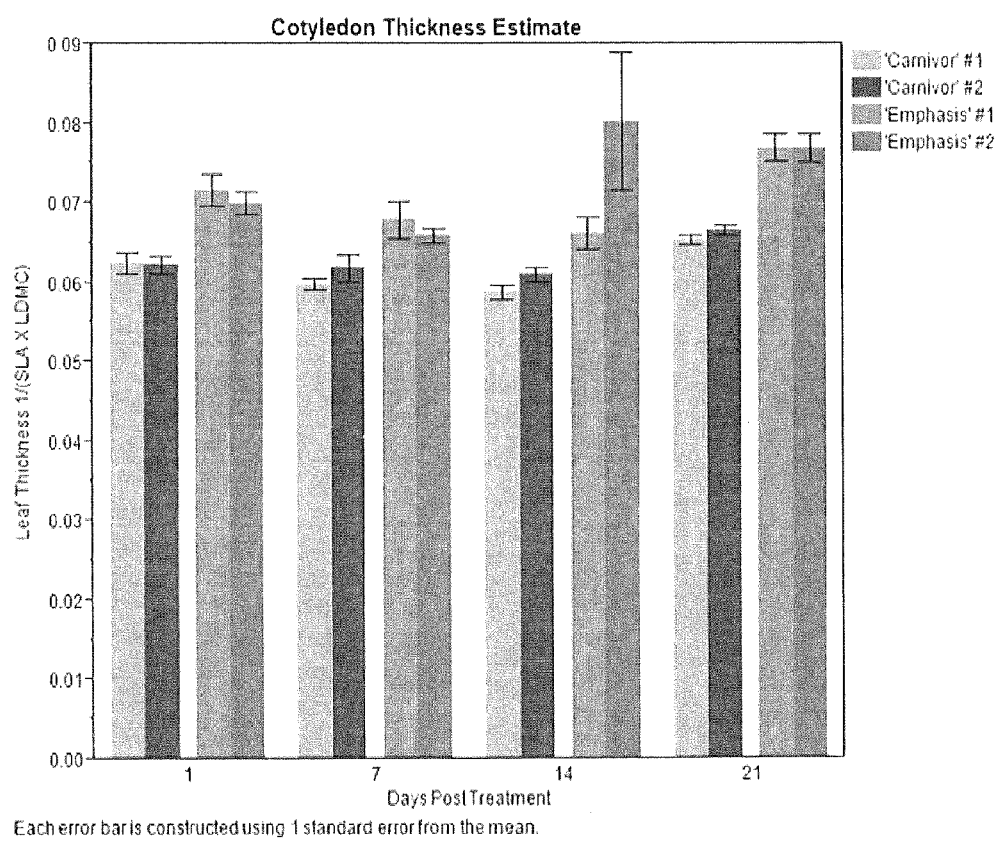
FIG. 12 shows a cotyledon thickness estimate for the 'Carnivor' interspecific hybrid squash and 'Emphasis' bottle gourd rootstock seedlings following treatment with the fatty alcohol.

Thus, in one aspect, the present invention provides a method of inhibiting the growth of a shoot apical meristem of a cucurbit plant, comprising contacting a shoot apical meristem (See, for example, FIG. 2) of the cucurbit plant with an effective amount of a composition comprising, consisting essentially of, or consisting of one or more fatty alcohols, thereby inhibiting the growth of the shoot apical meristem of the cucurbit plant. In some embodiments, the contacting can be done before and/or after grafting. In other embodiments, the cucurbit plant is a cucurbit rootstock plant.

In a further aspect, the present invention provides a method of preparing a cucurbit rootstock plant for grafting, comprising contacting a shoot apical meristem of a cucurbit rootstock plant with an effective amount of a composition comprising, consisting essentially of, or consisting of one or more fatty alcohols, thereby inhibiting the growth of the shoot apical meristem of the cucurbit rootstock plant, wherein inhibition of the shoot apical meristem prepares the rootstock for grafting.

In an additional aspect, the present invention provides a method of producing a cucurbit rootstock plant for grafting, comprising contacting a shoot apical meristem of a cucurbit rootstock plant with an effective amount of a composition comprising, consisting essentially of, or consisting of one or more fatty alcohols, thereby inhibiting the growth of the shoot apical meristem of the cucurbit rootstock plant and producing a cucurbit rootstock plant for grafting.

A further aspect of the present invention provides a method of producing a grafted cucurbit plant, comprising (a) preparing a cucurbit rootstock plant for grafting by contacting a shoot apical meristem of the cucurbit rootstock plant with an effective amount of a composition comprising, consisting essentially of, or consisting of one or more fatty alcohols prior to grafting; and (b) grafting a cucurbit scion onto the cucurbit rootstock plant of (a), thereby producing a grafted cucurbit plant.

In some aspects, a method of increasing the amount of at least one nonstructural carbohydrate in a cucurbit rootstock plant, comprising contacting a shoot apical meristem of the cucurbit rootstock plant with an effective amount of a composition comprising one or more fatty alcohols, thereby inhibiting the growth of the shoot apical meristem and increasing the amount of at least one nonstructural carbohydrate in the cucurbit rootstock plant. In some embodiments, the at least one nonstructural carbohydrate can comprise total nonstructural carbohydrates.

A further aspect of the invention provides a method of grafting a cucurbit scion onto a cucurbit rootstock plant, comprising (a) inhibiting the growth of a shoot apical meristem of the cucurbit rootstock plant by contacting a shoot apical meristem of the cucurbit rootstock plant with an effective amount of a composition comprising one or more fatty alcohols prior to grafting; and (b) grafting a cucurbit scion onto the cucurbit rootstock plant of (a).

In other aspects, the present invention provides a method of increasing grafting successor grafting success rate between a cucurbit rootstock plant and a cucurbit scion plant, comprising (a) inhibiting the growth of a shoot apical meristem of the cucurbit rootstock plant with an effective amount of a composition comprising one or more fatty alcohols; and (b) grafting a cucurbit scion onto the cucurbit rootstock plant of (a), wherein the grafting success or grafting success rate of the rootstock to the scion is increased as compared to a control in which growth of a shoot apical meristem of the cucurbit rootstock plant is not inhibited.

The terms "increase," "increasing," "increased," "enhance," "enhanced," "enhancing," and "enhancement" (and grammatical variations thereof), as used herein, describe an increase in the amount of at least one nonstructural carbohydrates in a cucurbit rootstock plant of at least about 1 fold to about 1000 fold (or about 0.1 µg to about 10 µg nonstructural carbohydrate) per hypocotyl and/or cotyledon and/or a increase in grafting success rate between a cucurbit rootstock plant and a cucurbit scion plant of at least about 5% to about 100% as compared to a control. Thus, in some embodiments, an increase in the amount of at least one nonstructural carbohydrate can be observed in a cucurbit rootstock plant prepared or produced using the methods of the invention by comparison to the amount in a control cucurbit rootstock plant. A control cucurbit rootstock plant can be an untreated cucurbit rootstock plant (e.g., a cucurbit rootstock plant not produced or prepared using the methods of this invention), and/or a cucurbit rootstock plant produced using the methods of the invention on day one of contact with a composition of fatty alcohols as described herein.

In other embodiments, grafting success between a cucurbit rootstock plant prepared or produced using the methods of the invention and a scion can be measured by comparison to the grafting success of a control cucurbit rootstock plant and a cucurbit scion plant. A control cucurbit rootstock plant can be a cucurbit rootstock plant that has not been prepared or produced using the methods of this invention. In some embodiments, grafting success can be observed between an individual grafted scion and rootstock plant as compared to a control rootstock plant grafted to a scion and/or grafting success can be as compared to a population of control grafted plants. Grafting success can be measured using factors that include, but are not limited to, the percentage of grafts that have healed (e.g., whether the graft can be pulled apart) and/or the amount of root regrowth.

Thus, in some embodiments, an increase in the amount of at least one nonstructural carbohydrate in a cucurbit rootstock plant can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000 fold increase, and the like, or any range therein, in the amount of at least one nonstructural carbohydrate per hypocotyl and/or cotyledon of a rootstock plant as compared to a control. In some embodiments, the increase in the amount of at least one nonstructural carbohydrate can be from about 3 fold to about 550 fold. In other embodiments, the increase in the amount of at least one nonstructural carbohydrates can be from about 5 fold to about 30 fold, and the like.

In other embodiments, an increase in the amount of at least one nonstructural carbohydrate in a cucurbit rootstock plant can be about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 10 µg, and the like, or any range therein, in the amount of the at least one nonstructural carbohydrate per hypocotyl and/or cotyledon of a rootstock plant as compared to a control.

In still other embodiments, an increase in grafting success (rate) between a cucurbit rootstock plant and a cucurbit scion plant can be a percent increase in grafting success of at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, and the like, or any range therein, as compared to a control. In some particular embodiments, an increase in grafting success between a cucurbit rootstock plant and a cucurbit scion plant can be at least about 25% to about 90%, or about 45% to about 85% increase in grafting success as compared to a control. In other embodiments, the grafting success is increased by about 50% as compared to a control. In still other embodiments, the grafting success is increased by about 80% as compared to a control.

As used herein, a successful graft refers to a graft between a rootstock plant and a scion plant that is healed and viable and/or root regrowth is observed. In some embodiments, a successful graft can be measured after a period of time following first grafting. In particular embodiments, the time period can be from about 5 to about 14 days (i.e., about 5, 6, 7, 8, 9, 10, 11, 12, 13, or 14 days) after first grafting.

As used herein, "grafting success" or "grafting success rate" is measured as the number of grafts that are healed and viable after a period time following first grafting as compared to the number that are not healed and viable after said time period. In some embodiments, the time period can be about from about 5 to about 10 days (i.e., about 5, 6, 7, 8, 9, or 10 days) after first grafting. In other embodiments, the time period can be from about 7 to about 10 days (e.g., 7, 8, 9, 10 days) after first grafting.

In additional embodiments, prior to grafting a rootstock plant having the growth of its shoot apical meristem inhibited as described herein can have one or all of the cotyledons removed. Previous to the present invention, it was believed that a hypocotyl cannot be viably grafted without cotyledons. Without wishing to be bound by any particular theory, it is hypothesize that grafting failure in the absence of the cotyledons was due to the need for the energy for graft healing; the energy being provided by the photosynthesis of the cotyledons. However, the removal of the meristem using the fatty alcohol treatment as described herein, as well as time following the application to allow the hypocotyl time to store carbohydrates, makes grafting without one or both cotyledons possible. The advantages of removing cotyledons prior to grafting include complete control of regrowth because of removal of meristem; more grafted plants can be placed in a tray (improved efficiency of grafting); and decreased disease probability in the healing chamber as there is less area for pooling of condensation.

As used herein, the term "nonstructural carbohydrate" refers to any carbohydrate that can be made available to the plant for energy use in graft healing. Thus, these are carbohydrates that are easily converted back into glucose and metabolized. Nonlimiting examples of nonstructural carbohydrates include glucose, sucrose, fructose, fructan, and starch. Methods for detecting nonstructural carbohydrates are known in the art (See, e.g., Zhao et al. (*Crop Science* 50:1537-1545 (2010)). The term "total nonstructural carbohydrate" is used herein when discussing as a group the nonstructural carbohydrates that were analyzed.

In some embodiments, contact of the composition comprising the fatty alcohols with the shoot apical meristem can be for about 1 hour to about 24 hours. In some particular embodiments, the contact of the composition comprising the fatty alcohols with the shoot apical meristem can be for about 1 hour to about 12 hours. In still other embodiments, contact of the composition comprising the fatty alcohols with the shoot apical meristem can be for about 1 hour to about 6 hours. Thus, contact of the composition comprising the fatty alcohols with the shoot apical meristem can be for about 1, 2, 3, 4, 5, 6, 7, 8, 9, 10, 11, 12, 13, 14, 15, 16, 17, 18, 19, 20, 21, 22, 23, 24 hours and the like or any range therein.

In some embodiments, following contact of the shoot apical meristem with the composition, the cucurbit plant can be incubated to allow time for the composition to kill the meristem and the plant rest prior to grafting to a scion. Thus, "incubate," "incubating," and "incubation" (and grammatical variations thereof) refer to the time between the contacting and when the rootstock can be used for grating to a scion (e.g., the time for the composition to inhibit/kill the rootstock apical meristem and for the treated plant to rest/recover before grafting to the scion). In representative embodiments, "incubating" can be for a time of about 4 hours to about 21 days after initial contact of the shoot apical meristem of the rootstock plant with the composition comprising the fatty alcohols. In some embodiments, the shoot apical meristem of rootstock plant is incubated for about 1 day to about 21 days following contact of the shoot apical meristem with said composition. In an additional embodiment, the shoot apical meristem can be incubated for about 5 to about 14 days after contact of the shoot apical meristem with said composition. In other embodiments, the shoot apical meristem of rootstock plant is incubated for about 5 to about 10 days after contact of the shoot apical meristem with said composition. In still other embodiments, the shoot apical meristem of rootstock plant is incubated for about 5 to about 7 days after contact of the shoot apical meristem with said composition.

Thus, in some embodiments of the invention, the shoot apical meristem of rootstock plant is incubated following contact with the composition of fatty alcohols for about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, or about 21 days.

Accordingly, in representative embodiments, a cucurbit scion can be grafted to a rootstock plant contacted with the fatty alcohol compositions as described herein at about 4 hours to about 21 days after first contacting the shoot apical meristem of said rootstock plant with a composition comprising one or more fatty alcohols. In some embodiments of the invention, a cucurbit scion can be grafted to a rootstock plant contacted with the fatty alcohol compositions as described herein at about 1 day to about 21 days after first contacting the shoot apical meristem of said rootstock plant with a composition comprising one or more fatty alcohols. In other embodiments, a cucurbit scion can be grafted to a rootstock plant contacted with the fatty alcohol compositions as described herein at about 5 days to about 7 days after first contacting the shoot apical meristem of said rootstock plant with a composition comprising one or more fatty alcohols.

Thus, in some embodiments of the invention, a cucurbit scion can be grafted to a rootstock plant contacted with the fatty alcohol compositions as described herein at about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, or about 21 days after initial contact of the shoot apical meristem of said rootstock plant with said composition.

Any suitable cucurbit rootstock plant can be used with this invention. Non-limiting examples of a cucurbit rootstock plant include a wild watermelon rootstock plant (*Citrullus lanatus* subsp. *lanatus, Citrullus lanatus* subsp. *mucosospermus*), a bottle gourd rootstock plant (e.g., *Lagenaria* spp., *Lagenaria siceraria*), an interspecific squash rootstock plant (e.g., *Cucurbita maxima*×*Cucurbita moschata*), a figleaf gourd (e.g., *Cucurbita ficifolia*) plant, wax gourd (*Benincasa hispida*) plant, a *C. moschata* plant, a *Cucumis hystrix* Chakrav plant, a *Cucumis hytivus* J. F. Chen & J. H. Kirkbr. plant, a *Cucumis metuliferus* E. Mey. ex Naud. plant, a *Cucumis melo* plant, and/or other wild-type cucurbit plant (e.g., *C. lanatus, Citrulus lanatus* subsp *lanatus* 'Ojakkyo'; *Cucumis africanus; Cucumis myriocarpus*).

Additionally, any cucurbit scion plant suitable for use with a cucurbit rootstock plant described herein can be used with this invention. Thus, in some embodiments, a cucurbit scion plant includes, but is not limited to, a watermelon (*Citrullus lanatus* subsp. *vulgaris*) scion, a melon scion (*Cucumis melo*), an oriental melon scion (*Cucumis melo* var. *makuwa*) or a cucumber scion (*Cucumis sativus*).

Thus, in representative embodiments the present invention provides a bottle gourd rootstock plant and a watermelon (*Citrullus lanatus*) scion. In other embodiments, the present invention provides an interspecific squash rootstock plant and watermelon scion (*Citrullus lanatus*), a melon scion (*Cucumis melo*), an oriental melon scion (*Cucumis melo* var. *makuwa*) or a cucumber scion (*Cucumis sativus*). In further embodiments, the present invention provides a figleaf gourd rootstock plant (*Cucurbita ficifolia*) and a cucumber scion. In still further embodiments, the present invention provides a Cucurbita moschata rootstock plant and a cucumber scion or a watermelon scion. In some embodiments of the invention, the cucurbit rootstock plant is wild watermelon (*Citrullus lanatus* subsp. *lanatus, Citrullus lanatus* subsp. *mucosospermus, Citrullus colocynthis*) and the scion is a watermelon plant (*Citrullus lanatus* subsp *vulgaris*). In other embodiments, the present invention provides a *Cucumis* melo rootstock plant and a melon scion. In still other embodiments, the cucurbit rootstock plant is a wax gourd (*Benincasa hispida*) plant and the scion is a watermelon plant.

Any suitable method of contacting the fatty alcohol composition to the cucurbit rootstock shoot apical meristem can be used with the methods of this invention, wherein growth of the shoot apical meristem is inhibited but optionally in which the cotyledons remain substantially intact and can support the growth of a grafted scion plant. Accordingly, non-limiting methods of contacting the fatty alcohol composition to the cucurbit rootstock shoot apical meristem include applying droplets to the shoot apical meristem of the seedling, "painting" the solution onto cucurbit rootstock shoot apical meristem, spraying or misting the rootstock plants with the fatty alcohol composition such that the composition drips down into the shoot apical meristem, and/or dipping cucurbit rootstock seedlings in a fatty alcohol composition, wherein the composition drips down into the shoot apical meristem when the plant is uprighted after dipping. It is noted that the cotyledons of cucurbit rootstock plants are waxy and therefore, hydrophobic. Further, some species of rootstock plants have trichomes on the epidermis that reduces absorption of the fatty alcohol composition. As such, a fatty alcohol composition applied to a cucurbit rootstock plant will roll off the cotyledons toward the shoot apex, coming to rest on the shoot apical meristem area, leaving the cotyledons with little or no damaged but burning or killing the shoot apical meristem. In some representative embodiments, the cotyledons of the rootstock plant are partially or fully removed. Thus, in some embodiments, the rootstock plant has one cotyledon remaining. In other embodiments, the rootstock plant has no cotyledons remaining.

Thus, in representative embodiments, contacting the composition comprising, consisting essentially of, or consisting of one or more fatty alcohols to a shoot apical meristem of a cucurbit rootstock plant comprises applying one or more droplets of the composition comprising, consisting essentially of, or consisting of one or more fatty alcohols to the shoot apical meristem of the rootstock plant. In some embodiments of the invention, a droplet can be a volume of about 0.25 µl to about 500 µl, or any range therein. In other embodiments, a droplet can be a volume of about 1 µl to about 250 µl or any range therein. In still other embodiments, a droplet can be a volume of about 5 µl to about 50 µl, or any range therein. Accordingly, in some embodiments, a droplet can be a volume of about 0.25 µl, about 0.5 µl, about 0.75 µl, about 1 µl, about 2 µl, about 3 µl, about 4 µl, about 5 µl, about 6 µl, about 7 μl, about 8 μl, about 9 μl, about 10 μl, about 11 μl, about 12 μl, about 13 μl, about 14 μl, about 15 μl, about 16 μl, about 17 μl, about 18 μl, about 19 μl, about 20 μl, about 25 μl, about 30 μl, about 35 μl, about 40 μl, about 45 μl, about 50 μl, about 55 μl, about 60 μl, about 65 μl, about 70 μl, about 75 μl, about 80 μl, about 85 μl, about 90 μl, about 95 ml, about 100 μl, about 125 μl, about 150 μl, about 175 μl, about 200 μl, about 225 μl, about 250 μl, about 275 μl, about 300 μl, about 325 μl, about 350 μl, about 375 μl, about 400 μl, about 425 μl, about 450 μl, about 475 μl, and/or about 500 μl, and the like. In particular embodiments, the droplet can be about 20 μl.

In representative embodiments, the total concentration of the one or more fatty alcohols in the composition that is contacted (as a droplet, paint, spray, mist, and the like) with the shoot apical meristem can be about 2.0% (volume/volume (v/v)) to about 40% (v/v) fatty alcohol, and any range therein. In other embodiments, the range of the concentration of the one or more fatty alcohols in the composition can be about 2.0% (v/v) to about 30% (v/v) fatty alcohol, about 2.0% (v/v) to about 20% (v/v) fatty alcohol, about 3.0% (v/v) to about 5% (v/v) fatty alcohol. Thus in some embodiments, the concentration of one or more fatty alcohols in the composition that is contacted with the shoot apical meristem of the cucurbit root stock can be about 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10%, 10.5%, 11%, 11.5%, 12%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5%, 20%, 20.5%, 21%, 21.5%, 22%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30%, 30.5%, 31%, 31.5%, 32%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40% (volume/volume), and the like, or any combination thereof.

In representative embodiments, the general structure of a fatty alcohol is

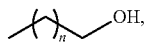

wherein n=number of carbons. In some embodiments of the invention, n=6 to 20. In other embodiments of the invention, n=6 to 12. In some embodiments, the one or more fatty alcohols can be one or more saturated fatty alcohols, unsaturated fatty alcohols, or a combination thereof. In particular embodiments, the one or more fatty alcohols can be one or more saturated fatty alcohols.

In some embodiments, the composition comprising, consisting essentially or, consisting of one or more fatty alcohols, comprises, consists essentially of, or consists of N-hexanol fatty alcohol ($C_6$), N-heptanol ($C_7$) fatty alcohol, N-octanol ($C_8$) fatty alcohol, N-nonanol ($C_9$) fatty alcohol, N-decanol ($C_{10}$) fatty alcohol, N-undecanol ($C_{11}$) fatty alcohol, N-dodecanol ($C_{12}$), N-tridecanol ($C_{13}$) fatty alcohol, N-tetradecanol ($C_{14}$) fatty alcohol, N-pentadecanol ($C_{15}$) fatty alcohol, N-hexadecanol ($C_{16}$) fatty alcohol, N-heptadecanol ($C_{17}$) fatty alcohol, N-octadecanol ($C_{18}$) fatty alcohol, N-nonadecanol ($C_{19}$) fatty alcohol, N-eicosanol ($C_{20}$) fatty alcohol, and/or any combination thereof. In further embodiments, the composition comprising, consisting essentially or, consisting of one or more fatty alcohols, comprises, consists essentially of, or consists of N-hexanol ($C_6$) fatty alcohol, N-octanol ($C_8$) fatty alcohol, N-decanol ($C_{10}$) fatty alcohol and N-dodecanol ($C_{12}$) fatty alcohol. In still further embodiments, the composition comprising, consisting essentially or, consisting of one or more fatty alcohols, comprises, consists essentially of, or consists of N-octanol ($C_8$) fatty alcohol and N-decanol ($C_{10}$) fatty alcohol. In other embodiments, the composition comprising, consisting essentially or, consisting of one or more fatty alcohols, comprises, consists essentially of, or consists of N-decanol ($C_{10}$) fatty alcohol. In additional embodiments, the composition comprising, consisting essentially or, consisting of one or more fatty alcohols, comprises, consists essentially of, or consists of N-octanol ($C_8$) fatty alcohol. In further embodiments, the fatty alcohols useful with the invention as described herein are saturated fatty alcohols, unsaturated fatty alcohols, or a combination thereof. In some embodiments, the individual and/or the total fatty alcohols can be present in the composition in the concentrations described above.

In still further embodiments, the one or more fatty alcohols in the composition for inhibition of the cucurbit rootstock apical meristem can be provided by FAIR 85® (Fair Products, Inc., Cary, N.C.), Offshoot-T® (Chemtura Corp., Middlebury, Conn.), Sucker Plucker®(Drexel Chemical Co., Memphis Tenn.), Antak® (Drexel Chemical Co., Memphis Tenn.), Royaltac® (Chemtura Corp., Middlebury, Conn.), Fairtac C-10® (Fair Products, Inc., Cary, N.C.), and the like, or any combination thereof. In some embodiments, the concentration of the one or more fatty alcohols in a composition, wherein the fatty alcohols are provided by FAIR 85®, Offshoot-T®, Sucker Plucker®, Antak®, Royaltac®, Fairtac C-10®, or combination thereof, can be about 2% to about 40% (v/v), about 2% (v/v) to about 30% (v/v) fatty alcohol, about 2% (v/v) to about 20% (v/v) fatty alcohol, about 3% (v/v) to about 5% (v/v), about 2% (v/v) to about 6% (v/v) and/or about 3% (v/v) to about 5% (v/v) fatty alcohol as described herein for fatty alcohol compositions useful for this invention. Thus, in some embodiments, the concentration of the one or more fatty alcohols in a composition can be about 2%, 3%, 4%, 5%, 6%, 7%, 8%, 9%, 10%, 11%, 12.0%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40% (v/v), and the like, and any range therein. In a representative embodiment, the concentration of the one or more fatty alcohols in a composition can be about 5.3% (v/v) (6.25% of Fair 85). In other embodiments, concentration of total fatty alcohols in a composition can be about 2.3% (v/v).

An "effective" amount of a fatty alcohol composition as used herein, is an amount of the fatty alcohol compound or composition that is sufficient to achieve the intended effect, i.e., to inhibit shoot apical meristem growth in a cucurbit rootstock. An effective amount may vary with particular factors that are within the knowledge and expertise of those skilled in the art. Thus, for example, as the person skilled in the art of grafting cucurbit plants would know, the morphological characteristics of the particular rootstock species or cultivar being treated can affect the amount/concentration of a fatty alcohol composition needed to inhibit shoot apical meristem growth in said cucurbit rootstock plant. Such morphological characteristics include, but are not limited to, the degree of hydrophobicity of the surface of the cotyledons (amount of epidermal wax), the presence and quantity/concentration of epidermal hairs (trichomes) and/or the morphology of the apical meristem of the particular rootstock species being treated. An "effective amount" of the fatty alcohols for use in inhibiting shoot apical meristem growth of a cucurbit rootstock plant can be readily determined by one of ordinary skill in the art. In some embodiments, an effective amount of a fatty alcohol composition comprises, consists essentially of, or consists of a total fatty alcohol concentration about 2.0% to about 40% (v/v) as described herein, wherein the fatty alcohol can be N-hexanol fatty alcohol ($C_6$), N-heptanol ($C_7$) fatty alcohol, N-octanol ($C_8$) fatty alcohol, N-nonanol ($C_9$) fatty alcohol, N-decanol ($C_{10}$) fatty alcohol, N-undecanol ($C_{11}$) fatty alcohol, N-dodecanol ($C_{12}$), N-tridecanol ($C_{13}$) fatty alcohol, N-tetradecanol ($C_{14}$) fatty alcohol, N-pentadecanol ($C_{15}$) fatty alcohol, N-hexadecanol ($C_{16}$) fatty alcohol, N-heptadecanol ($C_{17}$) fatty alcohol, N-octadecanol ($C_{18}$) fatty alcohol, N-nonadecanol ($C_{19}$) fatty alcohol, N-eicosanol ($C_{20}$) fatty alcohol, and/or any combination thereof.

In representative embodiments, the cucurbit rootstock shoot apical meristem is contacted with the fatty alcohol composition during the time period from when the cucurbit rootstock plant's cotyledons open until the appearance of the first true leaf. In some embodiments, the cucurbit rootstock apical meristem is contacted with the fatty alcohol composition at about 5 days to about 10 days after sowing or seeding, or any range therein. Thus, in some embodiments, the shoot apical meristem is contacted with the fatty alcohol composition at about 5 days to about 9 days after sowing or seeding, or about 5 days to about 7 days after sowing or seeding. Thus, in some embodiments, the shoot apical meristem is contacted with the fatty alcohol composition at about 5 days, about 6 days, about 7 days, about 8 days, about 9 days, or about 10 days and the like, after seeding or sowing.

In some embodiments, a composition comprising one or more fatty alcohols is contacted with the rootstock apical meristem prior to grafting. Typically, one application of the fatty alcohol composition prior to grafting is sufficient to inhibit the shoot apical meristem growth of the rootstock plant. In other embodiments, a rootstock plant that is not contacted with a fatty alcohol composition prior to grafting can be contacted after the grafting of the scion to the rootstock to inhibit the shoot apical meristem of the rootstock plant post-grafting. For example, once the graft between the rootstock and the scion is healed, the shoot apical meristem of the rootstock can be contacted with a composition comprising, consisting essentially of, or consisting of one or more fatty alcohols. Accordingly, in some embodiments, the shoot apical meristem of the grafted rootstock plant can be contacted with the composition comprising, consisting essentially of or consisting of one or more fatty alcohols at about 5 days to about 9 days after grafting (e.g., about 5 days, about 6 days, about 7 days, about 8 days, about 9 days, and the like after grafting).

In representative embodiments, a diluent or main carrier of a composition of one or more fatty alcohols as described herein is water, and/or water comprising, for example, a surfactant (e.g., soapy water), or other agriculturally acceptable carrier. An agriculturally-acceptable carrier can include natural or synthetic, organic or inorganic material which is combined with the active component to facilitate its application to the plant, or part thereof. In representative embodiments, an agriculturally-acceptable carrier includes, but is not limited to inert components, dispersants, surfactants, adjuvants, tackifiers, stickers, binders, or combinations thereof, that can be used in agricultural formulations. The concentration of agriculturally acceptable carriers and/or inert ingredients can be about 0% to about 15% of the total composition.

Accordingly, in some embodiments, the compositions comprising one or more fatty alcohols can be mixed with one or more agriculturally acceptable carriers and prepared by various means, e.g., by homogeneously mixing, blending and/or grinding the composition(s) with suitable carriers using conventional formulation techniques.

The compositions of the present invention can be made in any formulation suitable for inhibiting a cucurbit rootstock shoot apical meristem. Such formulations include, but are not limited to, a spray, a suspension, a mist, an aerosol, a foam, paste, and combinations thereof.

In particular aspects of the present invention, compositions comprising one or more fatty alcohols can be used in combination with additional active compounds. Thus, in some embodiments, compositions comprising one or more fatty alcohols further comprise additional active compounds. In other embodiments, the additional active compounds can be provided in one or more than one composition that is separate from the compositions comprising one or more fatty alcohol. Additional active compounds that are useful in combination with a composition comprising one or more fatty alcohols includes, but is not limited to, fertilizers, plant nutrients and micronutrients, amino acids, plant hormones and hormone-like compounds, pesticides, fungicides, insecticides, nematicides, reflective materials, and the like.

The present invention further provides cucurbit rootstock plants and plant parts and grafted cucurbit plants produced using the methods described herein.

The present invention is more particularly described in the following examples that are intended as illustrative only since numerous modifications and variations therein will be apparent to those skilled in the art.

EXAMPLES

Example 1

Inhibition of the Shoot Apical Meristem of Cucurbit Rootstock (Species Here)

Rootstock plants, bottle gourd (*Lagenaria siceraria* var. 'Emphasis') or interspecific hybrid squash (*C. maxima*×*C. moschata* var. 'Carnivor'), were sown in Fafard 3-b fertilizer-free mix and allowed to germinate. At the point when the cotyledons unfolded, (approx. 5-10 days after seeding) a droplet of a composition comprising fatty alcohols was applied to the shoot apical meristem of the seedling, between the cotyledons, so that the meristem was covered with solution. The fatty alcohol composition comprised a concentration of total fatty alcohols of about 2.3% (volume/volume) and was made by diluting the fatty alcohol product, FAIR 85®, 1:19 or 1:24 with water. The droplet volume was 20 to 500 μL and was applied with a pipette (20-200 μL or 1000 μL volume capability, using plastic tips). Seedlings were watered prior to treatment, to avoid needing to water post-treatment, which can dilute or wash away the fatty alcohol solution and prevent burnout of the shoot apical meristem. The treated rootstock seedlings can then be grafted to the appropriate scion at about 1 to 21 days post-treatment. In this case, the rootstock seedling was grafted to a cucurbit scion at about 24 hours after the rootstock shoot apical meristem was first contacted with the fatty alcohol composition.

Example 2

Preparation of a Grafted Cucurbit Plant (Species Here) Using a Cucurbit Rootstock Plant from Example 1

Grafting can be performed at about 1-21 days after a rootstock shoot apical meristem is treated with a fatty alcohol solution. Possible grafting methods include the following: 1) hole-insertion, in which the rootstock meristem is removed, a hole is punched into the old meristematic area with a bamboo needle, and the scion (cut at the end to both sharpen and expose vascular cambium tissue) is inserted into the prepared rootstock; and 2) one cotyledon, where the rootstock's meristem area and one cotyledon are removed, and the cut scion hypocotyl is adjoined to the resulting wound, stabilized with a clip, and allowed to heal. Once grafted, the plants are placed for approximately seven days in a healing chamber under high humidity for about the first 1-3 days, and then gradually decreasing humidity for the remaining days. After about seven days of healing, the grafted plants can be removed from the chamber and planted.

In this case, the cucurbit rootstock seedling as described in Example 1 was grafted to a cucurbit scion, watermelon (*Citrullus lanatus* subsp. *vulgaris* cv. 'Tri-X-313') or melon (*Cucumis melo* cv. 'Athena') at about 24 hours after the rootstock shoot apical meristem was first contacted with the fatty alcohol composition. Seven days were allowed for the graft to heal. Out of a total of 2016 grafts performed over 1800 (90-100%) were successful and all exhibited death of the rootstock meristem.

Example 3

Results of Treating Cucurbit Rootstock Apical Shoot Meristems Using Maleic Hydrazide, Sulphuric Acid or Oryzalin Chemical Means Other than Fatty Alcohol Compositions The same rootstock and scion species were used in this example as in Examples 1 and 2.

Maleic Hydrazide.

Maleic hydrazide (21.7%; Royal MH-30®; Chemtura Corp., Middlebury, Conn.) at a concentration of about 90 mg/ml was applied to the shoot apical meristem of rootstock plant. The treated rootstock plants were incubated for about 24 hours prior to grafting to a scion.

Similar to fatty alcohols solutions, maleic hydrozide solutions are used to inhibit tobacco sucker growth. However, in the case of the inhibition of shoot meristem growth in cucurbit rootstock plants, maleic hydrazide was found not only to inhibit apical meristem growth but it was also found to inhibit grafting as no grafts were successful when maleic hydrazide was used. Thus, out of 2016 attempted grafts, 100% inhibition of meristematic growth was observed but no successful grafts were observed.

Oryzalin.

Oryzalin or Surflan AS (Dow AgroSciences), a herbicide for annual grasses and broadleaf weeds, was applied to the shoot apical meristem of the cucurbit rootstock plant at a concentration of about 10 times the rate suggested on the label (i.e., about 10 mM). The treated rootstock plants were incubated with the Oryzalin for about 24 hours prior to grafting. Out of 2016 attempted grafts, over 1800 of the grafts were successful (90-100%). However, even at rates of up to 10× the recommended amount, Oryzalin was only able to stunt but not stop the apical meristem from growing. Thus, zero percent meristem inhibition was observed.

Sulfuric Acid.

Sulfuric acid at a concentration of about 18N to about 9N was applied to the shoot apical meristem of the cucurbit rootstock plant. The treated rootstock plants were incubated with the sulfuric acid for about 24 hours prior to grafting. Application of sulfuric acid resulted in death of the shoot apical meristem but in addition, the grafting tissues were also destroyed. Thus, out of 2016 attempted grafts none were successful.

Example 4

Fatty Alcohol Treatment to Increase Total Non-Structural Carbohydrates in Cucurbit Rootstock After treatment with fatty alcohols ("blinding"), it was observed that rootstocks increase in size and the hypocotyls and cotyledons become longer and thicker. Thus, in addition to removing the meristem and preventing rootstock regrowth, chemical decapitation of the rootstock using fatty alcohol treatment as described above may allow the rootstock to store more carbohydrates in the hypocotyl, thus resulting in an increased graft success rate.

To quantify these observations, seedlings of bottle gourd (e.g., 'Emphasis' bottle gourd; Syngenta Seeds, Boise Id.) and interspecific hybrid squash (e.g., 'Carnivor' Interspecific Hybrid Squash) were planted in 72-cell trays (72 plants per treatment) and treated with a dilute fatty alcohol solution (6.25% Fair 85; Fair Chemicals, Inc.) at the point when the cotyledons first unfolded (about 6-10 days after planting). Seedlings were harvested on 1, 7, 14, and 21 days post treatment. Hypocotyls and cotyledons were harvested and the following measurements were taken: fresh weight, dry weight, length, width, and cotyledon area. Leaf Thickness was estimated according to the following formula (Vile et al. *Annals of Botany* 96: 1129-1136 (2005)): $(SLA \times LDMC)^{-1}$, wherein SLA=Specific Leaf Area (leaf area/leaf dry mass) and LDMC=Leaf Dry Matter Content (leaf dry mass/fresh mass).

To determine the total nonstructural carbohydrate content, tissue was dried in an oven at 50° C. for 72 hours and hypocotyl and cotyledon dry weights were taken. The dried hypocotyls or cotyledons of five plants were combined, ground, and frozen until assayed. Seventy mg of tissue was used to assay for total nonstructural carbohydrates (TNC) according to the protocol of Zhao et al. (*Crop Science* 50:1537-1545 (2010)). In brief, Glucose, Sucrose, and Fructose were purified via an 80% ethanol extraction and activated charcoal filtration. Fructan was extracted from the ethanol-soluble solution via an acid digest in 0.2 M acetic acid. Following ethanol extraction, starch was enzymatically extracted from the original sample residue and separated into glucose units. Fructose, sucrose, and fructan were enzymatically converted to glucose and Glucose (HK) Assay Kit (GAHK) reagent (includes enzymes and other reagents used to determine the concentrations of glucose) was added and absorbance at 340 nm was measured. Concentrations were determined by use of a standard curve, sugar amount per gram hypocotyl was calculated using the dry weight of the tissue, and average hypocotyl weight was used to calculate the amount of TNC per hypocotyl. The controls were plants were seedlings harvested on day one.

The results are shown in Tables 1-5 and FIGS. 3-15.

TABLE 1

Amount of glucose per hypocotyl versus cotyledon.

| | ug Glucose per g dried tissue | | | | | | | |
|---|---|---|---|---|---|---|---|---|
| | Carnivor | | | | Emphasis | | | |
| | Hypocotyl | | Cotyledon | | Hypocotyl | | Cotyledon | |
| Day | Rep 1 | Rep 2 | Rep 1 | Rep 2 | Rep 1 | Rep 2 | Rep 1 | Rep 2 |
| 1 | 0.21 | 0.59 | 0.1 | 0.7 | 0.21 | 0.34 | 0.05 | 0.24 |
| 7 | 0.31 | 1.44 | 0.99 | 2.06 | 0.43 | 0.64 | 0.55 | 1.26 |
| 14 | 1.96 | 2.12 | 1.08 | 1.36 | 0.87 | 0.74 | 0.78 | 1.22 |
| 21 | 2.71 | 2.11 | 0.99 | 1.1 | 0.98 | 0.86 | 0.99 | 1.05 |
| Increase | 13.21 | 3.6 | 10.54 | 2.95 | 4.66 | 2.55 | 19.3 | 5.35 |
| Difference | 2.5 | 1.52 | 0.98 | 1.36 | 0.77 | 0.52 | 0.93 | 1.03 |

TABLE 2

Amount of sucrose per hypocotyl versus cotyledon.

| | ug Sucrose per g dried tissue | | | | | | | |
|---|---|---|---|---|---|---|---|---|
| | Carnivor | | | | Emphasis | | | |
| | Hypocotyl | | Cotyledon | | Hypocotyl | | Cotyledon | |
| Day | Rep 1 | Rep 2 | Rep 1 | Rep 2 | Rep 1 | Rep 2 | Rep 1 | Rep 2 |
| 1 | 0.18 | 0.30 | 0.05 | 0.99 | 0.07 | 0.05 | 0.08 | 0.32 |
| 7 | 0.19 | 0.29 | 0.36 | 1.12 | 0.1 | 0.07 | 0.12 | 0.51 |
| 14 | 0.47 | 0.56 | 0.89 | 1.89 | 0.21 | 0.31 | 0.35 | 1.14 |
| 21 | 0.64 | 0.54 | 1.11 | 2.47 | 0.47 | 0.21 | 0.52 | 1.24 |
| Increase | 3.55 | 1.84 | 20.38 | 2.5 | 6.73 | 5.8 | 6.8 | 3.87 |
| Difference | 0.46 | 0.25 | 1.05 | 1.48 | 0.4 | 0.25 | 0.44 | 0.92 |

TABLE 3

Amount of fructose per hypocotyl versus cotyledon.

| | ug Fructose per g dried tissue | | | | | | | |
|---|---|---|---|---|---|---|---|---|
| | Carnivor | | | | Emphasis | | | |
| | Hypocotyl | | Cotyledon | | Hypocotyl | | Cotyledon | |
| Day | Rep 1 | Rep 2 | Rep 1 | Rep 2 | Rep 1 | Rep 2 | Rep 1 | Rep 2 |
| 1 | 0.28 | 0.44 | 0.18 | 0.38 | 0.11 | 0.2 | 0.04 | 0.11 |
| 7 | 0.33 | 0.65 | 0.92 | 0.75 | 0.21 | 0.31 | 0.38 | 0.55 |
| 14 | 0.7 | 1.01 | 1.06 | 0.74 | 0.35 | 0.45 | 0.49 | 0.55 |
| 21 | 0.87 | 1.13 | 0.77 | 0.52 | 0.56 | 0.5 | 0.49 | 0.6 |
| Increase | 3.12 | 2.55 | 6.18 | 1.98 | 3.17 | 2.55 | 13.06 | 5.34 |
| Difference | 0.59 | 0.69 | 0.89 | 0.37 | 0.29 | 0.3 | 0.45 | 0.49 |

TABLE 4

Amount of starch per hypocotyl versus cotyledon.

ug Starch per g dried tissue

|  | Carnivor | | | | Emphasis | | | |
| --- | --- | --- | --- | --- | --- | --- | --- | --- |
|  | Hypocotyl | | Cotyledon | | Hypocotyl | | Cotyledon | |
| Day | Rep 1 | Rep 2 | Rep 1 | Rep 2 | Rep 1 | Rep 2 | Rep 1 | Rep 2 |
| 1 | 0.05 | 0.07 | -0.002 | 0.16 | 0.01 | 0.03 | 0.005 | 0.08 |
| 7 | 1.21 | 3.67 | 1.52 | 2.92 | 0.07 | 0.29 | 1.13 | 2.08 |
| 14 | 4.37 | 5.44 | 2.74 | 3.2 | 0.24 | 0.7 | 2.025 | 2.52 |
| 21 | 7.33 | 8.15 | 4.25 | 4.03 | 0.41 | 1.04 | 2.91 | 4.07 |
| Increase | 153.11 | 111.4 | 2.8 | 25.28 | 37.31 | 36.3 | 540.68 | 50.48 |
| Difference | 7.28 | 8.08 | 4.25 | 3.87 | 0.4 | 1.01 | 2.9 | 3.99 |

TABLE 5

Amount of total nonstructural carbohydrate per hypocotyl versus cotyledon.

ug TNC components per g dried tissue

|  | Carnivor | | | | Emphasis | | | |
| --- | --- | --- | --- | --- | --- | --- | --- | --- |
|  | Hypocotyl | | Cotyledon | | Hypocotyl | | Cotyledon | |
| Day | Rep 1 | Rep 2 | Rep 1 | Rep 2 | Rep 1 | Rep 2 | Rep 1 | Rep 2 |
| 1 | 0.64 | 1.4 | 0.33 | 2.23 | 0.4 | 0.61 | 0.17 | 0.75 |
| 7 | 2.03 | 6.04 | 3.79 | 6.85 | 0.75 | 1.29 | 2.09 | 4.41 |
| 14 | 6.4 | 9.12 | 5.78 | 7.18 | 1.67 | 2.2 | 3.63 | 5.42 |
| 21 | 9.72 | 11.92 | 7.12 | 8.12 | 2.43 | 2.61 | 4.9 | 6.96 |
| Increase | 15.04 | 8.49 | 21.74 | 3.65 | 6.09 | 4.25 | 28.81 | 9.27 |
| Difference | 9.08 | 10.52 | 6.79 | 5.89 | 2.02 | 2 | 4.73 | 6.21 |

Each table contains the results from two planting dates. In each case, date 1 (6 Aug. 2012) is shown in the first column (Rep 1) and date 2 (17 Sep. 2012) is shown in the second column (Rep 2). The row labeled "Increase" shows the result of the highest result/lowest result to give an idea of the multiplicity of the increase. The row labeled "Difference" illustrates the difference between the highest concentration and Day 1. Any negative values were calculated as zero. Tables 1-3 show ethanol-soluble sugars. The results were negative for fructan, which is not a sugar produced by cucurbits (data not showns). Table 4 shows the results for starch, which shows the greatest increase. Table 5 shows the sum of sugars and starch multiplied by the average hypocotyl or cotyledon weight to illustrate the amount of sugar available in the average hypocotyl or cotyledon. A significant increase is evident for all treatments.

As can be seen in FIGS. 3-12, both cotyledon and hypocotyl sizes (length and width) as well as fresh and dry weights increased as a result of the treatment with the fatty alcohols in both bottle gourd and interspecific hybrid squash rootstocks.

Figure 13:
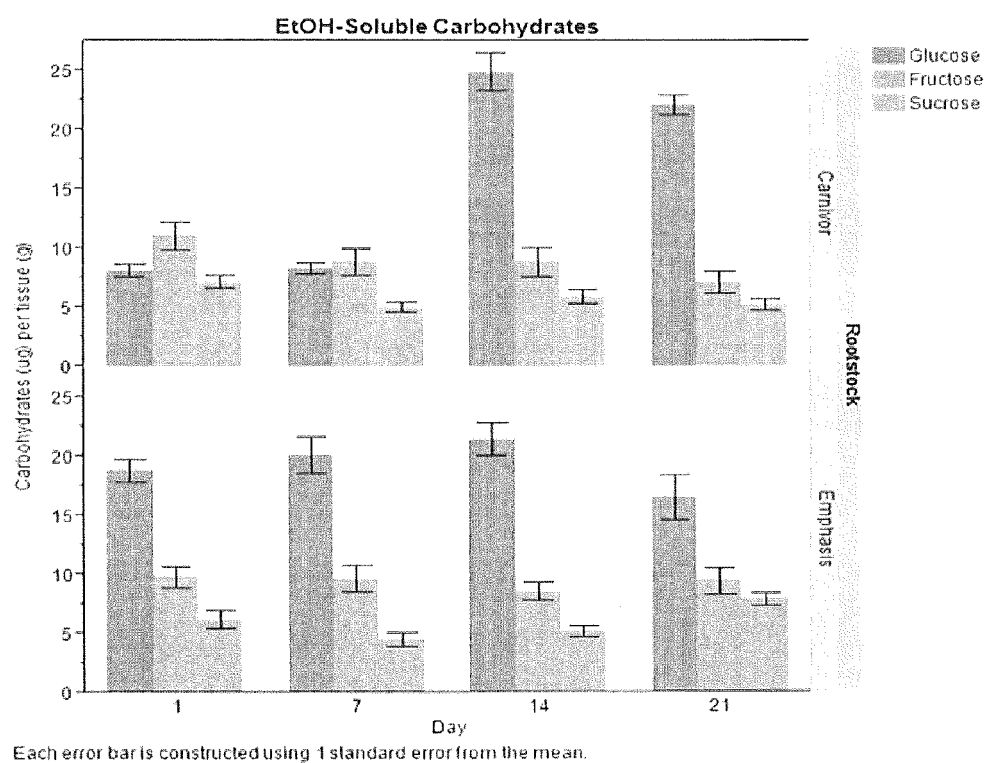
FIG. 13 shows the amount of ethanol (EtOH) soluble carbohydrates for the 'Carnivor' interspecific hybrid squash and 'Emphasis' bottle gourd rootstock seedlings following treatment with the fatty alcohol.
Figure 14:
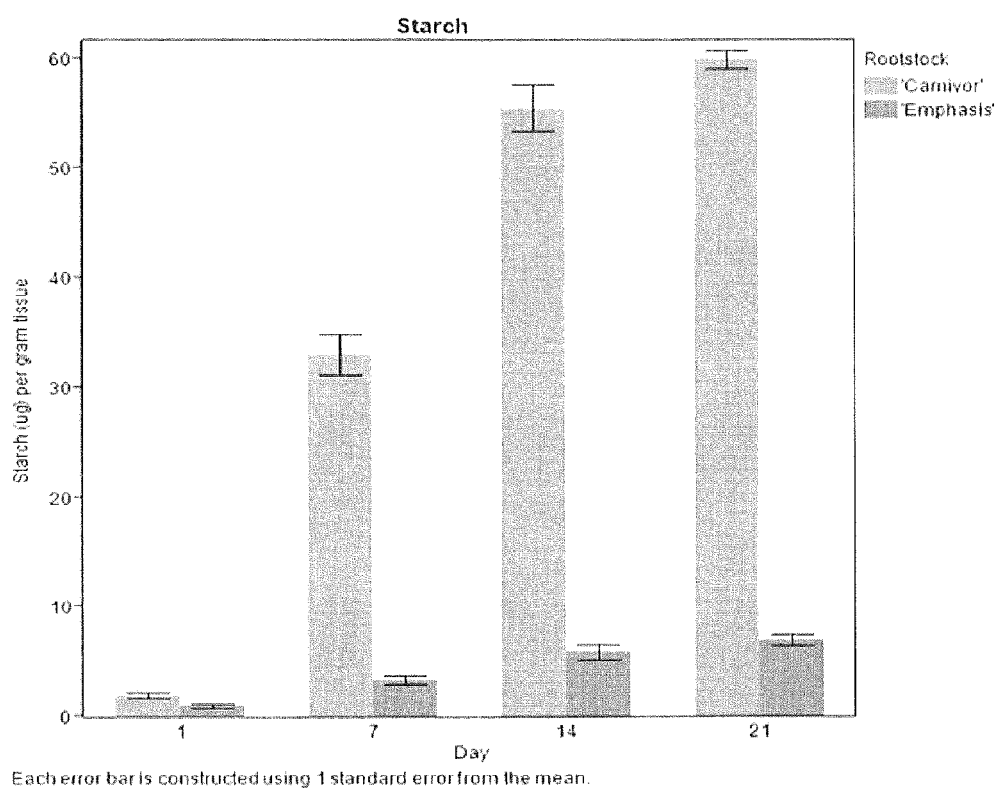
FIG. 14 shows the starch content for the 'Carnivor' interspecific hybrid squash and 'Emphasis' bottle gourd rootstock seedlings following treatment with the fatty alcohol.
Figure 15:
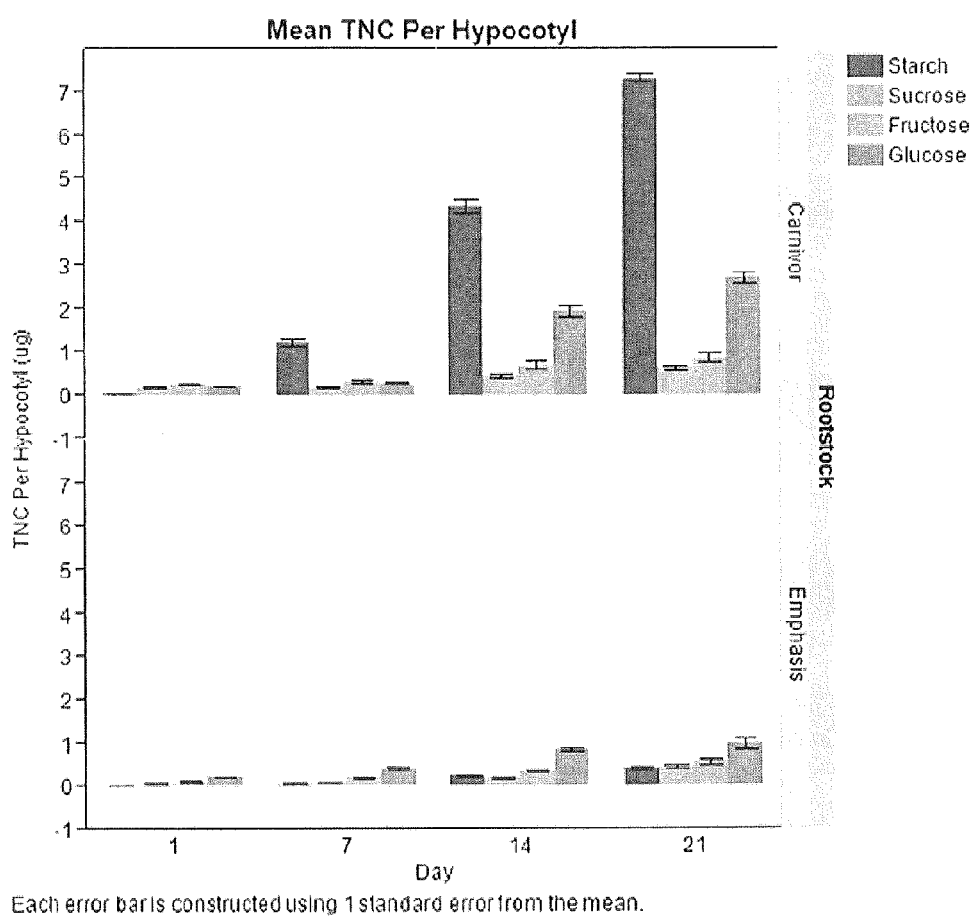
FIG. 15 shows the mean total nonstructural carbohydrates for the 'Carnivor' interspecific hybrid squash and 'Emphasis' bottle gourd rootstock seedlings following treatment with the fatty alcohol.

Rep 1 data from Tables 1-5 are shown in FIGS. 13-15. FIG. 13 and FIG. 14 illustrate the raw concentration of four TNC (glucose, fructose, sucrose, and starch) observed in the plant hypocotyls over time. As noted above, the results for fructans are not shown, as the analysis yielded no result. A significant increase in μg glucose per gram tissue over time is seen for both bottle gourd and interspecific hybrid rootstocks, with the peak glucose concentration occurring on day 14 following fatty alcohol treatment. This increase is more significant in the interspecific hybrid than in the bottle gourd. Although sucrose levels decrease on day seven, no significant increase or decrease over time is shown in fructose or sucrose per gram tissue. As shown in FIG. 14, of the TNC components analyzed, starch concentration (μg starch/g tissue) increases most significantly.

FIG. 15 combines the TNC concentrations (FIGS. 13 and 14) with the average hypocotyl dry weight (FIG. 4) to illustrate the observed increase in average amount of TNC per hypocotyl. Each TNC component shows a significant increase over the 21-day testing period, with the interspecific hybrid rootstock showing a greater increase than the bottle gourd. Of the nonstructural carbohydrates, the amount of glucose and starch increased the most dramatically. The increase observed in total nonstructural carbohydrate, as well as the increase observed in rootstock seedling size, illustrates the effectiveness of the use of fatty alcohols for not only removing the meristem and preventing rootstock regrowth, but also for allowing the rootstock seedlings to store more carbohydrates in the hypocotyl, which can lead to an increased graft success rate.

The foregoing is illustrative of the present invention, and is not to be construed as limiting thereof. The invention is defined by the following claims, with equivalents of the claims to be included therein.

All publications, patent applications, patents and other references cited herein are incorporated by reference in their entireties for the teachings relevant to the sentence and/or paragraph in which the reference is presented.

The invention claimed is:

1. A method of inhibiting the growth of a shoot apical meristem of a cucurbit plant, comprising
    contacting a shoot apical meristem of the cucurbit plant with an effective amount of a composition comprising one or more fatty alcohols during the time period from when the cucurbit plant's cotyledons open until the appearance of the first true leaf, thereby inhibiting the growth of the shoot apical meristem of the cucurbit plant.

2. A method of producing a cucurbit rootstock plant for grafting, comprising
contacting a shoot apical meristem of a cucurbit rootstock plant with an effective amount of a composition comprising one or more fatty alcohols, thereby inhibiting the growth of the shoot apical meristem of the cucurbit rootstock plant and producing a cucurbit rootstock plant for grafting.

3. A method of producing a grafted cucurbit plant, comprising
(a) contacting a shoot apical meristem of a cucurbit rootstock plant with an effective amount of a composition comprising one or more fatty alcohols prior to grafting; and
(b) grafting a cucurbit scion onto the cucurbit rootstock plant of (a), thereby producing a grafted cucurbit plant.

4. A method of increasing the amount of at least one nonstructural carbohydrate in a cucurbit rootstock plant, comprising
contacting a shoot apical meristem of the cucurbit rootstock plant with an effective amount of a composition comprising one or more fatty alcohols during the time period from when the cucurbit rootstock plant's cotyledons open until the appearance of the first true leaf, thereby inhibiting the growth of the shoot apical meristem and increasing the amount of at least one nonstructural carbohydrate in the cucurbit rootstock plant.

5. The method of claim 1, wherein the composition comprises N-hexanol fatty alcohol ($C_6$), N-octanol ($C_8$) fatty alcohol, N-decanol ($C_{10}$) fatty alcohol, N-dodecanol ($C_{12}$), N-tetradecanol, or any combination thereof.

6. The method of claim 3, wherein the composition comprises N-hexanol fatty alcohol ($C_6$), N-octanol ($C_8$) fatty alcohol, N-decanol ($C_{10}$) fatty alcohol, N-dodecanol ($C_{12}$), N-tetradecanol, or any combination thereof.

7. The method of claim 1, wherein the composition comprises N-octanol ($C_8$) fatty alcohol and/or N-decanol ($C_{10}$) fatty alcohol.

8. The method of claim 3, wherein the composition comprises N-octanol ($C_8$) fatty alcohol and/or N-decanol ($C_{10}$) fatty alcohol.

9. The method of claim 6, wherein the composition comprising one or more fatty alcohols comprises FAIR 85®, Offshoot-T®, Sucker Plucker®, or any combination thereof.

10. The method of claim 1, wherein the composition comprises a concentration of 2% (volume/volume) to about 40% (volume/volume) of fatty alcohols or about 2% (volume/volume) to about 20% (volume/volume) of fatty alcohols.

11. The method of claim 3, wherein the composition comprises a concentration of 2% (volume/volume) to about 40% (volume/volume) of fatty alcohols or about 2% (volume/volume) to about 20% (volume/volume) of fatty alcohols.

12. The method of claim 1, wherein the cucurbit plant is a wild watermelon rootstock plant, a bottle gourd rootstock plant, an interspecific squash rootstock plant, figleaf gourd, wax gourd, *C. moschata, Cucumis hystrix* Chakrav. *Cucumis hytivus* J. F. Chen & J. H. Kirkbr., *Cucumis metuliferus* E. Mey. ex Naud., *Cucumis melo*, and/or other wild-type cucurbit.

13. The method of claim 3, wherein the cucurbit rootstock plant is a wild watermelon rootstock plant, a bottle gourd rootstock plant, an interspecific squash rootstock plant, figleaf gourd, wax gourd, *C. moschata, Cucumis hystrix* Chakrav. *Cucumis hytivus* J. F. Chen & J. H. Kirkbr., *Cucumis metuliferus* E. Mey. ex Naud., *Cucumis melo*, and/or other wild-type cucurbit.

14. The method of claim 13, wherein the bottle gourd rootstock plant is *Lagenaria* spp. or *Lagenaria siceraria*, the interspecific squash rootstock plant is *Cucurbita maxima*× *Cucurbita moschata*, the figleaf gourd is *Cucurbita ficifolia*, the wax gourd is *Benincasa hispida* and the wild-type cucurbit is *C. lanatus, Citrullus lanatus* subsp. *lanatus* 'Ojakkyo', *Citrullus lanatus* subsp. *mucosospermus, Cucumis africanus*, or *Cucumis myriocarpus*.

15. A method of grafting a cucurbit scion onto a cucurbit rootstock plant, comprising
(a) inhibiting the growth of a shoot apical meristem of a cucurbit plant according to the method of claim 1, wherein the cucurbit plant is a cucurbit rootstock plant; and
(b) grafting a cucurbit scion onto the cucurbit rootstock plant of (a).

16. A method of increasing the grafting success rate between a cucurbit rootstock plant and a cucurbit scion plant, comprising
(a) inhibiting the growth of a shoot apical meristem of a cucurbit plant according to the method of claim 1 prior to grafting, wherein the cucurbit plant is a cucurbit rootstock plant; and
(b) grafting a cucurbit scion onto the cucurbit rootstock plant of (a), wherein the grafting success rate of the rootstock to the scion is increased.

17. The method of claim 15, wherein the composition comprises N-hexanol fatty alcohol ($C_6$), N-octanol ($C_8$) fatty alcohol, N-decanol ($C_{10}$) fatty alcohol, N-dodecanol ($C_{12}$), N-tetradecanol, or any combination thereof.

18. The method of claim 16, wherein the composition comprises N-hexanol fatty alcohol ($C_6$), N-octanol ($C_8$) fatty alcohol, N-decanol ($C_{10}$) fatty alcohol, N-dodecanol ($C_{12}$), N-tetradecanol, or any combination thereof.

19. The method of 15, wherein the rootstock plant is a wild watermelon rootstock plant, a bottle gourd rootstock plant, an interspecific squash rootstock plant, figleaf gourd, wax gourd, *C. moschata, Cucumis hystrix* Chakrav., *Cucumis hytivus* J. F. Chen & J. H. Kirkbr., *Cucumis metuliferus* E. Mey. ex Naud., *Cucumis melo*, and/or other wild-type cucurbit.

20. The method of 16, wherein the rootstock plant is a wild watermelon rootstock plant, a bottle gourd rootstock plant, an interspecific squash rootstock plant, figleaf gourd, wax gourd, *C. moschata, Cucumis hystrix* Chakrav., *Cucumis hytivus* J. F. Chen & J. H. Kirkbr., *Cucumis metuliferus* E. Mey. ex Naud., *Cucumis melo*, and/or other wild-type cucurbit.

21. The method of claim 20, wherein the bottle gourd rootstock plant is *Lagenaria* spp. or *Lagenaria siceraria*, the interspecific squash rootstock plant is *Cucurbita maxima*× *Cucurbita moschata*, the figleaf gourd is *Cucurbita ficifolia*, the wax gourd is *Benincasa hispida* and the wild-type cucurbit is *C. lanatus, Citrullus lanatus* subsp. *lanatus* 'Ojakkyo', *Citrullus lanatus* subsp. *mucosospermus, Cucumis africanus*, or *Cucumis myriocarpus*.

22. The method of claim 16, wherein the cucurbit rootstock is a bottle gourd plant and the scion is a watermelon plant (*Citrullus lanatus* subsp. *lanatus*).

23. The method of claim 16, wherein the cucurbit rootstock plant is an interspecific squash rootstock plant and the scion is a watermelon plant (*Citrullus lanatus* subsp. *lanatus* or *Citrullus lanatus* subsp. *mucosospermus*)), a melon plant (*Cucumis melo*), an oriental melon plant (*Cucumis melo* var. *makuwa*) or a cucumber plant (*Cucumis sativus*).

24. The method of claim 16, wherein the cucurbit rootstock plant is a figleaf gourd plant and the scion is a cucumber plant.

25. The method of claim 16 wherein the cucurbit rootstock plant is *Cucurbita moschata* and the scion is a cucumber plant or a watermelon plant.

26. The method of claim 16, wherein the cucurbit rootstock plant is wild watermelon (*Citrullus lanatus* subsp. *lanatus* or *Citrullus lanatus* subsp. *mucosospermus*) and the scion is a watermelon plant.

27. The method of claim 16, wherein the cucurbit rootstock plant is *Cucumis melo* var. *makuwa* and the scion is a melon plant.

28. The method of claim 16, wherein the cucurbit rootstock plant is wax gourd and the scion is a watermelon plant.

* * * * *

UNITED STATES PATENT AND TRADEMARK OFFICE
CERTIFICATE OF CORRECTION

| | | |
|---|---|---|
| PATENT NO. | : 8,629,330 B2 | Page 1 of 1 |
| APPLICATION NO. | : 13/762002 | |
| DATED | : January 14, 2014 | |
| INVENTOR(S) | : Hassell et al. | |

It is certified that error appears in the above-identified patent and that said Letters Patent is hereby corrected as shown below:

On Title Page:
Item 71, Column 1, Applicant: Please add the applicant listed below:
-- Clemson University, Anderson, SC (US) --

In the Specification:
Column 11, Line 6: Please correct "about 95ml," to read -- about 95µl, --

Signed and Sealed this
Seventh Day of October, 2014

Michelle K. Lee
*Deputy Director of the United States Patent and Trademark Office*